US009789212B2

(12) United States Patent
Pease et al.

(10) Patent No.: US 9,789,212 B2
(45) Date of Patent: Oct. 17, 2017

(54) METHODS FOR DIAGNOSING AND MONITORING EOSINOPHILIC ESOPHAGITIS

(71) Applicant: UNIVERSITY OF UTAH RESEARCH FOUNDATION, Salt Lake City, UT (US)

(72) Inventors: Leonard F. Pease, Bountiful, UT (US); Hedieh Saffari, Salt Lake City, UT (US); Gerald J. Gleich, Salt Lake City, UT (US); Kristin M. Leiferman, Salt Lake City, UT (US); Kathryn A. Peterson, Salt Lake City, UT (US); Russell Morris Condie, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 294 days.

(21) Appl. No.: 14/402,070

(22) PCT Filed: May 17, 2013

(86) PCT No.: PCT/US2013/041595
§ 371 (c)(1),
(2) Date: Nov. 18, 2014

(87) PCT Pub. No.: WO2013/173716
PCT Pub. Date: Nov. 21, 2013

(65) Prior Publication Data
US 2015/0132221 A1 May 14, 2015

Related U.S. Application Data

(60) Provisional application No. 61/688,650, filed on May 18, 2012, provisional application No. 61/786,909, filed on Mar. 15, 2013.

(51) Int. Cl.
*A61K 51/00* (2006.01)
*A61M 36/14* (2006.01)
*A61K 51/04* (2006.01)
*A61K 51/08* (2006.01)

(52) U.S. Cl.
CPC .......... *A61K 51/0491* (2013.01); *A61K 51/08* (2013.01)

(58) Field of Classification Search
CPC ........ A61K 51/00; A61K 51/08; A61K 51/04; A61K 51/0491
USPC .......... 424/1.11, 1.65, 1.69, 1.81, 1.85, 1.89, 424/9.1, 9.2, 9.3, 9.4, 9.5, 9.6; 514/1, 1.1
See application file for complete search history.

(56) References Cited

U.S. PATENT DOCUMENTS

| 3,847,138 | A | * | 11/1974 | Gollub | A61M 5/1723 600/4 |
|---|---|---|---|---|---|
| 4,871,357 | A | | 10/1989 | Hsu et al. | |
| 5,146,928 | A | | 9/1992 | Esser | |
| 6,638,294 | B1 | | 10/2003 | Palmer | |
| 2005/0256533 | A1 | | 11/2005 | Roth et al. | |
| 2009/0012553 | A1 | | 1/2009 | Swain et al. | |
| 2010/0240965 | A1 | | 9/2010 | Furuta et al. | |

FOREIGN PATENT DOCUMENTS

| WO | WO-91/03236 A1 | 3/1991 |
|---|---|---|
| WO | WO-2007/067919 A2 | 6/2007 |
| WO | WO-2011/126984 A1 | 10/2011 |
| WO | PCT/US2013/034170 | 3/2013 |
| WO | PCT/US2013/041595 | 5/2013 |
| WO | WO-2013/173716 A2 | 11/2013 |

OTHER PUBLICATIONS

Abu-Ghazaleh RI, et al., "Eosinophil granule proteins in peripheral blood granulocytes," J Leukoc Biol. 1992, 52: 611-618.
Attwood SE, et al., "Esophageal eosinophilia with dysphagia. A distinct clinicopathologic syndrome," Dig Dis Sci 1993, 3 8(1): 109-116.
Esquerre JP, et al., "Kinetics of technetium-labeled heparin in thromboembolism: Preliminary Report," Int. J. Nucl. Med. Bioi., 1979:6 (4):215-220.
Fogg MI, et al., "Pollen and eosinophilic esophagitis," J Allergy Cin Immunol 2003, 112(4): 796-797.
Frigas E, et al., "Cytotoxic effects of the guinea pig eosinophil major basic protein on tracheal epithelium," Lab Invest 1980, 42: 35-43.
Gangotena F, et al., "Eosinophilic Esophagitis, Ringed Esophagus: The Diagnostic Conundrum," Am J Gastroenterol 2007, 102: S145-S146, Abstract 79.
Gleich GJ et al., "Biochemical and functional similarities between human eosinophil-derived neurotoxin and eosinophil cationic protein: homology with ribonuclease," Proc Nat/ Acad Sci USA, 1986, 83: 3146-3150.
Gleich GJ et al., "Comparative properties of the Charcot-Leyden crystal protein and the major basic protein from human eosinophils," J Clin Invest Mar. 1976, 57: 633-640.
Gleich, GJ et al., "Physiochemical and biological properties of the major basic protein from guinea pig eosinophil granules," J Exp Med 1974, 140: 313-332.
Gonsalves N et al., "Histopathologic variability and Endoscopic Correlates in Adults with Eosinophilic Esophagitis," Gastrointestinal Endosc., 2006, 64(3): 313-319.
Gonsalves N, Kahrilas P, "Eosinophilic Esophagitis in Adults," Am J Gastroenterol Clin N Am 2008, 37: 349-368.
Gonsalves N et al., "A Prospective Trial of Six Food Elimination Diet and Reintroduction of Causative Agents in Adults with Eosinophilic Esophagitis," Digestive Disease Week Presentation 2008, Abstract No. 727.

(Continued)

Primary Examiner — D L Jones
(74) Attorney, Agent, or Firm — Ballard Spahr LLP

(57) ABSTRACT

Disclosed are compositions and methods for diagnosing eosinophilic esophagitis in a subject. Also disclosed are methods for monitoring the course of eosinophilic esophagitis in a subject before, during, and after treatment.

15 Claims, 9 Drawing Sheets

(56) References Cited

OTHER PUBLICATIONS

Gonsalves N et al., "Prospective Clinical Trial of Six Food Elimination Diet or Elemental Diet in the Treatment of Adults with Eosinophilic Gastroenteritis," Digestive Disease Week Presentation 2009, Abstract No. S1861.

Gundel RH et al., "Human eosinophil major basic protein induces airway constriction and airway hyperresponsiveness in primates," J Clin Invest, 1991, 87: 14 70-14 73.

Hiebert LM, et al., "Tissue distribution and antithrombotic activity of unlabeled or C14-labeled porcine intestinal mucosal heparin following administration to rats by the oral route," Can J Physiol Pharmacol., 2000; 78: 307-320.

Hirash J, et al., "Heparin and low-molecular-weight heparin: mechanisms of action, pharmacokinetics, dosing, monitoring, efficacy, and safety," Chest. 2001, 119: 64S-94S.

ICRP, 2008. Radiation Dose to Patients from Radiopharmaceuticals—Addendum 3 to ICRP Publication 53. ICRP Publication 106. Ann. ICRP 38 (1-2).

Kagawalla AF et al., "Effect of 6 food Elimination diet on clinical and histologic outcomes in eosinophilic esophagitis," Clin Gastroenterol Hepatol, 2006, 4: 1097-1102.

Kato M et al., "Eosinophil infiltration and degranulation in normal human tissue," Anat Record 1998, 252: 418-425.

Kephart GM et al., "Marked deposition of eosinophil-derived neurotoxin in adult patients with eosinophilic esophagitis," Am J Gastroenterol, 2010, 105(2): 298-307.

Konikoff et al., "A Randomized, Double-blind, Placebo controlled trial of Fluticasone Propionate for Pediatric Eosinophilic Esophagitis," Gastroenterol, 2006, 131: 1381-1391.

Kulkarni PV, et al., "Modified technetium-99m heparin for the imaging of acute experimental myocardial infarcts," J Nucl Med. 1980, 21: 117-121.

Kulkarni PV, et al., "Technetium Labeled Heparin: Preliminary Report of a New Radiopharmaceutical with Potential for Imaging Damaged Coronary Ateries and Myocardium," J Nucl Med 1978, 19: 810-815.

Laforest MD, et al., "Pharmacokinetics and bio-distribution of technetium 99m labeled standard heparin and a low molecular weight heparin (enoxaparin) after intravenous injection in normal volunteers," British Journal of Haematology. 1991, 77(2): 201-208.

Levine et al., "Disease of the Esophagus: Diagnosis with Esophagography," Radiology 2005,237: 414-427.

Liacouras C, et al., "Eosinophilic Esophagitis: Updated Consensus Recommendations for children and adults," J Allergy Clin Immunol. 2011, 128(1): 3-20.

Liacouras CA et al., "Eosinophilic Esophagitis: a 10-year experience in 381 children," Clin Gastroenterol hepatol 2005, 3: 1198-1206.

Mackenzie S.H., "Eosinophilic Oesophagitis in Patients Presenting with Dysphagia—A Prospective Analysis," Aliment Pharmacal Therapeutics 2008, 28(9): 1140-1146.

Majdalani G, et al., "Kinetics of technetium-labeled heparin in hemodialyzed patients," Kidney Int. Supply, 1993, 41: S131-S134.

Markowitz J. et al., "Elemental Diet is Effective Treatment for Eosinophilic Esophagitis in Children and Adolescents," Am J Gastroenterol 2003, 98: 777-782.

Mishra A et al., "An etiological role for aeroallergens and eosinophils in experimental eosinophilic esophagitis," J Clin Invest 2001, 107: 83-90.

O'Donnell MC et al., "Activation of basophil and mast cell histamine release by eosinophil granule major basic protein," J Exp Med, 1983, 157: 1981-1991.

Odze, R. D., "Pathology of eosinophilic esophagitis: What the clinician needs to know," Am J Gastroenterol 2009, 104: 485-490.

Pasha, SF, et al., "Patient characteristics, clinical, endoscopic, and histologic findings in adult eosinophilic esophagitis: a case series and systematic review of the medical literature," Dis Esophagus 2007, 20 (4): 311-319.

Pentiuk, S et al., "Dissociation between symptoms and histological severity in pediatric eosinophilic esophagitis," J Pediatr Gastroenterol Nutr. 2009, 48: 152-160.

Peters MS et al., "Localization of human eosinophil granule major basic protein, eosinophil cationic protein, and eosinophil-derived neurotoxin by immunoelectron microscopy," Lab Invest 1986, 54: 656-662.

Peterson KA, et al., "Elemental Diet Induces Histologic Response in Adult Eosinophilic Esophagitis," Am J Gastroenterol 2013, 759-766.

Prasad, GA et al., "Secular trends in the epidemiology and outcomes of eosinophilic esophagitis in Olmsted County, Minnesota (1976-2007)," Digestive Disease Week, May 2008.

Saffari H, et al., "Patchy eosinophil distributions in an esophagectomy specimen from a patient with eosinophilic esophagitis: Implications for endoscopic biopsy," J Allergy Clin. Immunol. 2012, 130: 798-800.

Shah, A et al., "Histopathologic variability in Children with Eosinophilic Esophagitis," Am J Gastroenterol, 2009, 104(3): 716-721.

Straumann A, et al., "Natural history of primary eosinophilic esophagitis: a follow-up of 30 adult patients for up to 11.5 years," Gastroenterology 2003, 125: 1660-1669.

Swaminathan et al. (2005) Eosinophil-granule major basic protein, a C-type lectin, binds heparin, Biochemistry 44: pp. 14152-14158.

Talley NJ, et al, "Deposition of eosinophil granule major basic protein in eosinophilic gastroenteritis and celiac disease," Gastroenterology. 1992, 103: 137-145.

Tantibhaedhyangkul, U et al., "Increased Esophageal Regulatory T Cells and Eosinophil Characteristics in Children with Eosinophilic Esophagitis and Gastroesophageal Reflux Disease," Annals of Clinical & Laboratory Science 2009, 39: 99-107.

Wang FY et al., "Is there a seasonal variation in the incidence or intensity of allergic eosinophilic esophagitis in newly diagnosed children?" J Clin Gastroenterol Hepatol 2007, 41:451-453.

Wasmoen, TL et al., "Biochemical and amino acid sequence analysis of human eosinophil granule major basic protein," J Biol Chem 1988, 263: 12559-12563.

International Search Report and Written Opinion were mailed on Nov. 12, 2013 by the International Searching Authority for Application No. PCT/US2013/041595, which was filed May 17, 2013 and published as WO 2013/173716 on Nov. 21, 2013 (Applicant—Univ. of Utah Research Foundation // Inventor—Pease et al.)(9 pages).

International Preliminary Report on Patentability was mailed on Nov. 18, 2014 by the International Searching Authority for Application No. PCT/US2013/041595, which was filed May 17, 2013 and published as WO 2013/173716 on Nov. 21, 2013 (Applicant—Univ. of Utah Research Foundation // Inventor—Pease et al.)(7 pages).

International Search Report and Written Opinion were mailed on Jul. 1, 2013 by the International Searching Authority for Application No. PCT/US2013/034170, which was filed Mar. 27, 2013 and published as WO 2013/148883 on Oct. 3, 2013 (Applicant—Univ. of Utah Research Foundation // Inventor—Pease et al.)(11 pages).

International Preliminary Report on Patentability was mailed on Oct. 1, 2014 by the International Searching Authority for Application No. PCT/US2013/034170, which was filed Mar. 27, 2013 and published as WO 2013/148883 on Oct. 3, 2013 (Applicant—Univ. of Utah Research Foundation // Inventor—Pease et al.)(10 pages).

U.S. Appl. No. 61/786,909, filed Mar. 15, 2013, Leonard F. Pease et al. (Univ. of Utah Research Foundation).

U.S. Appl. No. 61/688,650, filed May 18, 2012, Leonard F. Pease et al. (Univ. of Utah Research Foundation).

U.S. Appl. No. 61/685,917, filed Mar. 27, 2012, Leonard F. Pease et al. (Univ. of Utah Research Foundation).

U.S. Appl. No. 61/744,167, filed Sep. 19, 2012, Leonard F. Pease et al. (Univ. of Utah Research Foundation).

* cited by examiner

METHODS FOR DIAGNOSING AND MONITORING EOSINOPHILIC ESOPHAGITIS

CROSS-REFERENCE TO RELATED APPLICATIONS

This application is a U.S. National Phase Application of International Application No. PCT/US2013/041595, filed May 17, 2013, which claims the benefit of U.S. Provisional Patent Application No. 61/688,650, filed on May 18, 2012, and U.S. Provisional Patent Application No. 61/786,909, filed on Mar. 15, 2013. The contents of the prior international and provisional applications are hereby incorporated by reference herein in their entirety.

STATEMENT REGARDING FEDERALLY SPONSORED RESEARCH

This invention was made with government support under R01 AI09728 awarded by the National Institutes of Health and CBET1125490 awarded by the National Science Foundation. The government has certain rights in the invention.

FIELD OF THE INVENTION

This invention relates generally to the field of diagnostics. Thus, disclosed are compositions and methods for diagnosing and monitoring eosinophil degranulation-associated esophagitis in a subject, using a radiolabeled contrast agent administered orally to a subject. Specifically, disclosed are compositions and methods for diagnosing and monitoring eosinophilic esophagitis in a subject, using radiolabeled heparin.

BACKGROUND

Eosinophilic esophagitis (EoE) is a chronic disease of the esophagus that affects over 300,000 patients in the U.S. alone. Symptoms include dysphagia (difficulty swallowing liquids or solids or both, >90%), food impaction (solid food sticks in the esophagus, 50%), odynophagia (painful swallowing), heartburn (33%), chest pain, asthma (50%), diarrhea, and vomiting (Gonsalves, Kahrilas, *Am J Gastroenterol*, 2009). The disease primarily occurs in males (75%) with a mean age between 36 and 42 years in westernized countries. While present in adults, the disease can also manifest in children. The symptoms of EoE are similar to an atopic allergenic inflammatory condition of the esophagus, affecting up to 10% of adults presenting for upper endoscopy (Mackenzie, *Aliment Ther Pharmacol, Gastroenterol*, 2008).

Although the source or sources of this disease have not been conclusively identified, investigators have identified several contributing factors. Genetic predisposition may be at work in this disease, at least in part, due to the increased incidence in first degree relatives of EoE patients relative to the general population. Environmental causes may also be important as allergens (i.e., food and aero-allergens) contribute in up to 97% of cases in children (Liacouras, *Clin Gastro Hep,* 2005). Fogg et al. (2003) observed worsening of EoE during the pollination season in an allergic patient. Wang et al. (2007) subsequently identified a seasonal variation in identification and severity of the disease in children. Furthermore, Mishra et al. (2001) determined that intranasal administration of *Aspergillus fumigatus* in a mouse model replicated the esophageal eosinophilic infiltrate seen in EoE. However, EoE is not simply a seasonal allergy of the esophagus. Despite current treatment with swallowed aerosolized steroids, the response rate is little better than 50% (Konikoff, *Gastroenterology,* 2007).

Food allergies also play an important role in both adult and pediatric EoE. Markowitz et al. (2003) found resolution of esophageal eosinophilia after 4 weeks of amino acid-based elemental diet in 49/51 pediatric patients. In the largest analysis to date, Liacouras et al. (2005) found a 97% response to an elemental diet in a cohort of 160 children with EoE. However, preliminary data on an elimination diet in adults found less robust responses than those observed in children. The six-food elimination diet (Gonsalves et al., 2012) demonstrated improvement in 78% and 33% complete resolution rate. Elemental diet in adults results in substantial improvement in eosinophilia after 4 weeks in 72% of patients (Peterson, 2013). Responses to skin prick testing in adults undergoing food elimination diets suggest a multimodal (IgE and non-IgE mediated) immunological process, and murine models find both aero-allergens and food each play significant roles (Mishra, *J Clin Invest,* 2001).

In all cases, detection of EoE via a form of endoscopy known as esophagoduodenoscopy (EGD) remains essential. In this procedure, a small tube with a camera on the distal end is passed into the esophagus, stomach, and first portion of the small intestine to visualize the mucosal surfaces of these organs. In EoE, the inflammation occurs in various parts of the esophagus; there is approximately equal incidence in the proximal, distal, or both portions of the esophagus being affected (Gangotena, *Am J Gastroenterol,* 2007) within cohorts, but such infiltrate varies in each individual with many demonstrating a less intense infiltrate proximally. EoE also affects the luminal structure of the esophagus. Pronounced rings or furrows can develop into strictures that close off the esophagus, resulting in odynophagia, dysphagia, food impaction, and emergency hospital visits. The areas of inflammation are not evenly distributed throughout an affected esophagus, as the disease often presents in patches or select segments of the 25-30 cm long adult esophagus.

Although EGD is a key tool in the identification of EoE, some cases may never present as a "ringed-esophagus" during EGD. A conclusive means currently available to clinicians to positively identify EoE is to detect the presence of eosinophils in biopsy specimens. Tissue samples may be collected during EGD and then examined with traditional histological analysis to confirm or reject a case of EoE. However, the patchy nature of the disease complicates collection of tissue samples for biopsy. When clinical suspicion for EoE is high, consensus practice requires sampling at 4 to 5 sites throughout the esophagus. However, five 2 mm biopsy specimens represent less than 0.7% of the 20- to 25-cm-long esophageal mucosa and might result in underdiagnosis of EoE if mucosal eosinophilia is particularly patchy. Specific disease phenotypes (i.e., rings, lines, furrows, white spots, or plaques) aid physicians in determining where and how many biopsies to perform based on EGD-observed phenotypes, which are strong indicators of eosinophil density. For example, biopsies to collect tissue samples are often collected from unaffected areas. For this reason, at least 4 (child) or 5 (adult) biopsy specimens are required to confirm each case of EoE (Gonsalves *Gastrointestinal Endosc,* 2006; Shah *Am J Gastroenterol,* 2009). Furthermore, additional biopsies are required to evaluate the effectiveness of each treatment proposed. This repeated need for endoscopic removal of tissue poses a financial hardship for the patient, and the procedure can be painful, requiring sedation and/or anesthesia.

The key element for diagnosing EoE in a biopsy specimen is the presence of eosinophils. Normal esophageal tissue does not contain eosinophils (Kato et al., 1998). These white blood cells were named for their affinity for the red dye eosin. Normally, eosinophils reside in the blood stream, stomach, small and large intestine, and lymphatic system (Kato et al., 1998) but infiltrate pathologically into the esophagus in EoE. In biopsy samples, an eosinophil can be identified as a cell 12-17 µm in diameter with a bi-lobed nucleus and cytoplasmic granules staining red with acidic dyes, for example eosin. A tissue count of eosinophils in excess of 15 per field of view at high microscope power (greater than 15 per high-powered field (hpf)) indicates EoE. Some clinical evidence suggests that inflammation increases with eosinophil concentration.

A distinctive characteristic of eosinophils is their granules which comprise markedly cationic proteins, each of which is composed of a core and a matrix. The core consists primarily of major basic protein 1 (MBP-1); the matrix consists of eosinophil peroxidase (EPO) and eosinophil derived neurotoxin (EDN) (Peters et al., 1986), inter alia. MBP-1 is a highly basic (isoelectric point approaching 12) 13.8 kDa protein with 5 unpaired cysteins that accounts for about 55% of the granule's protein (Gleich et al., 1974; Gleich et al., 1976). It is a member of the C-type lectin family (lectins bind sugars) and has the highest concentration in the eosinophil granule on a per molecule basis (Abu-Ghazaleh et al., 1992). EPO has the highest concentration in the granule on a per mass basis, while EDN and ECP are members of the RNAse 2 family (Gleich et al., 1986). Upon degranulation, an eosinophil releases each of these proteins into the surrounding tissues. Of these, only MBP-1 stimulates histamine release (O'Donnell et al., 1983). MBP-1 also exfoliates bronchial epithelial cells (Frigas et al., 1980) and causes bronchial hyper-reactivity (Gundel et al., 1991), whereas both MBP-1 and EPO provoke transient bronchial constriction (Gundel et al., 1991). These proteins are found in abundance in biopsies in eosinophilic esophagitis (Kephart, Am J Gastroenterol, 2010).

Currently, as symptoms are unable to predict the severity of eosinophilic involvement, the only way to adequately monitor the extent and severity of the disease is through invasive upper endoscopy with biopsy. Often, in food re-introduction and therapeutic evaluation, this results in several upper endoscopies per year for patients. Due to the cost, invasiveness, and discomfort experienced via this method of monitoring, patients become non-compliant, and subsequently the disease is not adequately tracked. Additionally, there is a lack of sensitivity of biopsies in detecting and understanding such a patchy disease because biopsies histologically characterize only <0.03% of the entire esophagus.

Despite the rapidly growing incidence of EoE, state-of-the-art diagnostic techniques remain inadequate to fully characterize this disease. As such, there exists a need to develop a non-invasive, precise, and comprehensive technique to image and map the distribution of inflammation and deposition of eosinophil granule proteins. Such techniques will provide a tool to diagnose EoE, track disease activity in response to various treatment regimens, and obtain previously unreachable insight into the development and progression of EoE pathophysiology.

SUMMARY

In accordance with the purposes of this invention, as embodied and broadly described herein, disclosed, in one aspect, is a method of producing a medical image of an esophagus in a subject, comprising detecting an eosinophil granule protein in the mucosal tissue of the esophagus in a subject, comprising administering to a subject radiolabeled heparin under conditions wherein the radiolabeled heparin can bind to an eosinophil granule protein, and detecting a radiolabeled heparin/eosinophil granule protein complex in the mucosal tissue of the esophagus, whereby detecting the radiolabeled heparin/eosinophil granule protein complex in the mucosal tissue of the esophagus produces a medical image of the esophagus in the subject.

In another aspect, disclosed is a method of diagnosing eosinophilic esophagitis or eosinophilic diseases in a subject, comprising detecting an eosinophil granule protein in the mucosal tissue of the esophagus or other organs in a subject, comprising administering to a subject radiolabeled heparin under conditions wherein the radiolabeled heparin can bind to an eosinophil granule protein, and detecting a radiolabeled heparin/eosinophil granule protein complex in the mucosal tissue of the esophagus or other organs, whereby detecting the radiolabeled heparin/eosinophil granule protein complex in the mucosal tissue of the esophagus diagnoses eosinophilic esophagitis or eosinophilic diseases in the subject.

In another aspect, disclosed is a method of detecting a change in eosinophilic esophagitis in a subject diagnosed with eosinophilic esophagitis, comprising: a) producing a first medical image of the esophagus in a subject diagnosed with eosinophilic esophagitis according to the disclosed methods, b) producing a second medical image of the esophagus in the subject of step (a) according to the disclosed methods, and c) comparing the medical image of step (b) with the medical image of step (a), whereby detecting a change in the medical image of step (b) compared to the medical image of step (a) detects a change in eosinophilic esophagitis in the subject.

In another aspect, disclosed is a method of detecting eosinophil degranulation in a subject, comprising detecting an eosinophil granule protein in a subject, comprising administering to a subject radiolabeled heparin under conditions wherein the radiolabeled heparin can bind to an eosinophil granule protein, and detecting a radiolabeled heparin/eosinophil granule protein complex, whereby detecting the radiolabeled heparin/eosinophil granule protein complex detects the presence of eosinophil degranulation in the subject.

BRIEF DESCRIPTION OF THE DRAWINGS

The accompanying figures, which are incorporated in and constitute a part of this specification, illustrate several aspects and together with the description serve to explain the principles of the invention.

Figure 4:
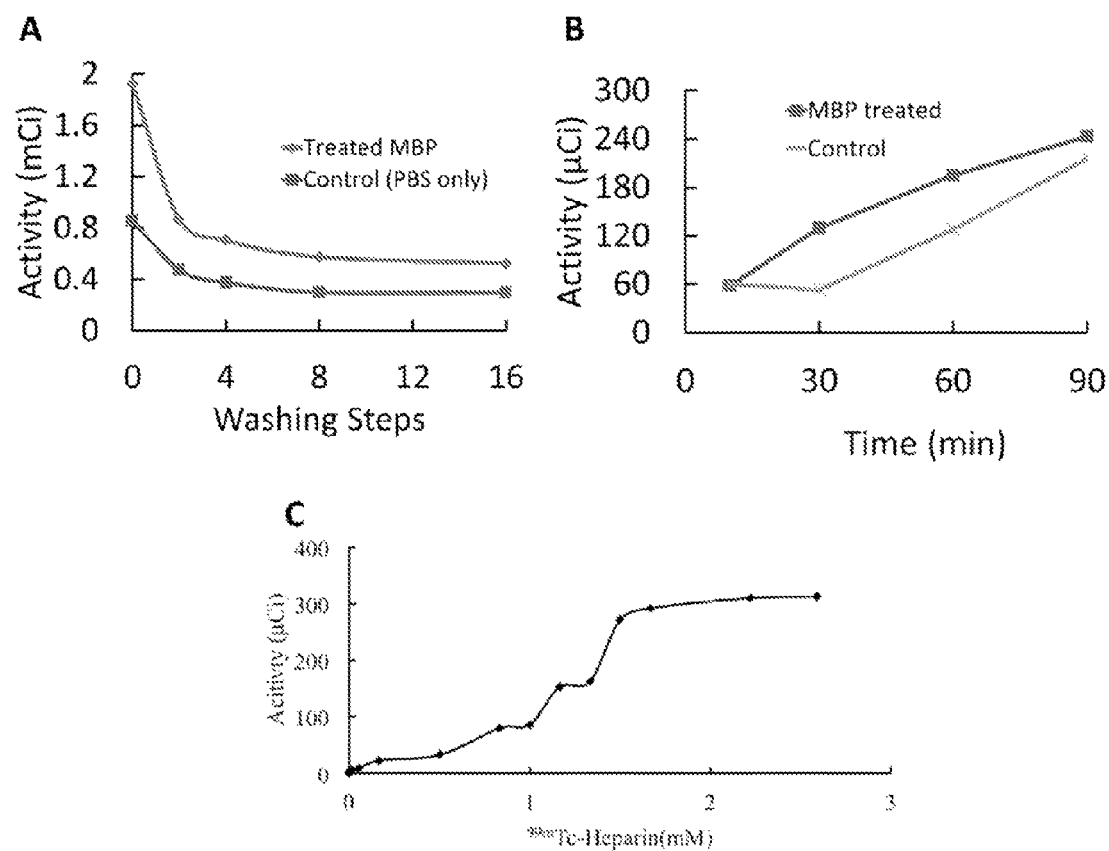

FIG. 4 shows $^{99m}$Tc-heparin binding to monkey esophagus biopsy tissue. (A) Shows a high level of initial activity of samples treated with MBP-1 compared to control. The level of activity decreases with subsequent washes before leveling out above control after the fourth wash. (B) Shows the effect of time on activity in samples treated with MBP-1. (C) Shows that activity within a sample reaches a saturation point between 1 and 2 mM treatment with $^{99m}$Tc-heparin.

Figure 5:
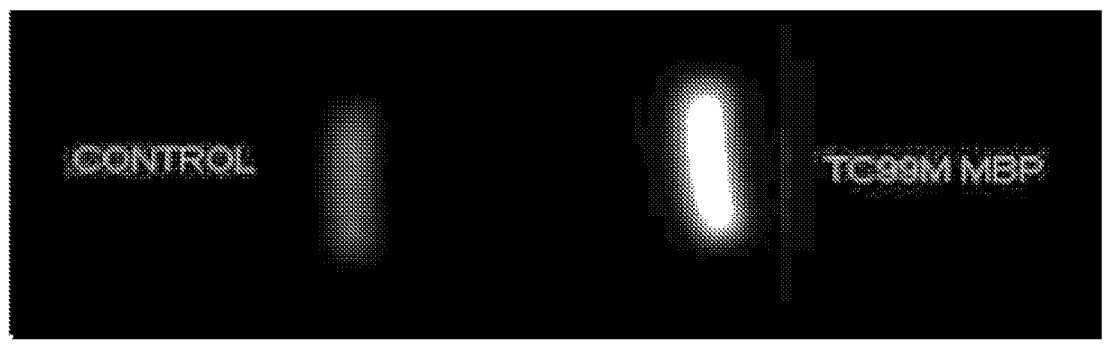

FIG. 5 shows a SPECT intensity image of a sample of monkey esophageal tissue. The monkey esophagus was incubated overnight with PBS (control) or MBP-1 (treated). Following this initial control versus treated incubation, the samples were incubated with $^{99m}$Tc-heparin. The representative result clearly demonstrates that $^{99m}$Tc-heparin intensity is significantly higher in the MBP-1-treated monkey esophageal tissue.

Figure 6:
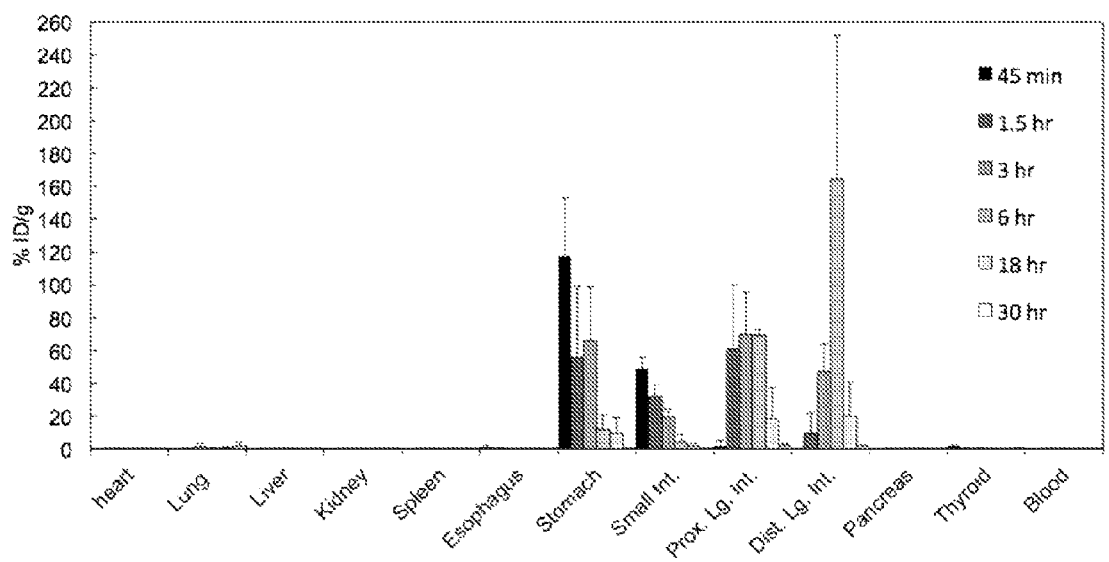

FIG. 6 shows ex vivo biodistribution of orally administered $^{99m}$Tc-heparin as measured using a well counter at different time points. Mean and standard deviation of % ID/g were corrected for physical decay of the isotope.

Figure 7:
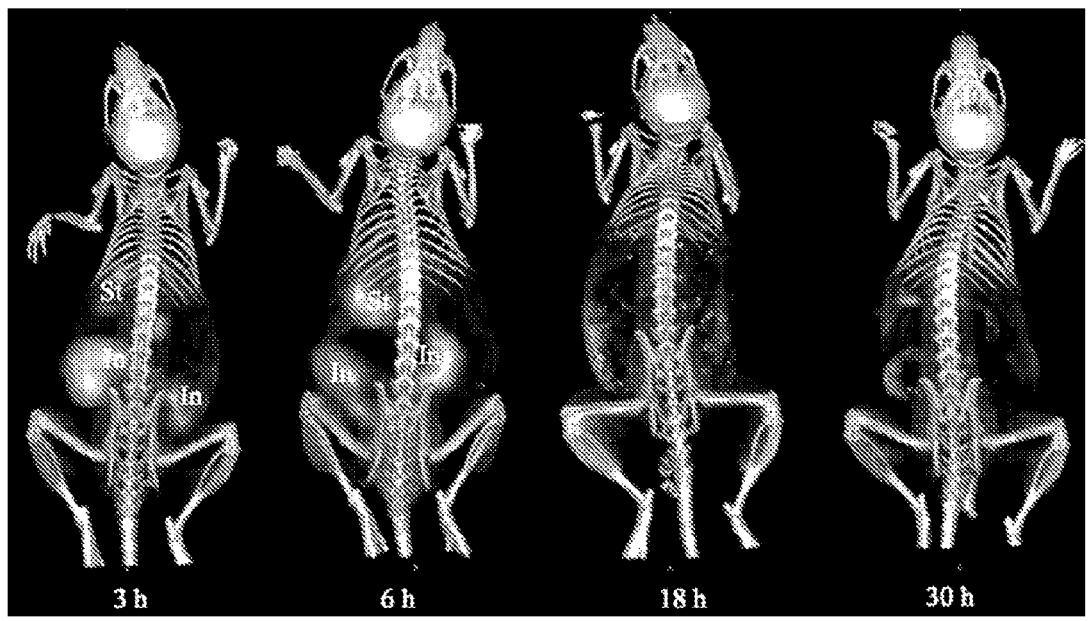

FIG. 7 shows SPECT/CT images of orally administered $^{99m}$Tc-heparin into mice at 3, 6, 18, and 30 hours. St=stomach; In=Intestines.

Figure 8:
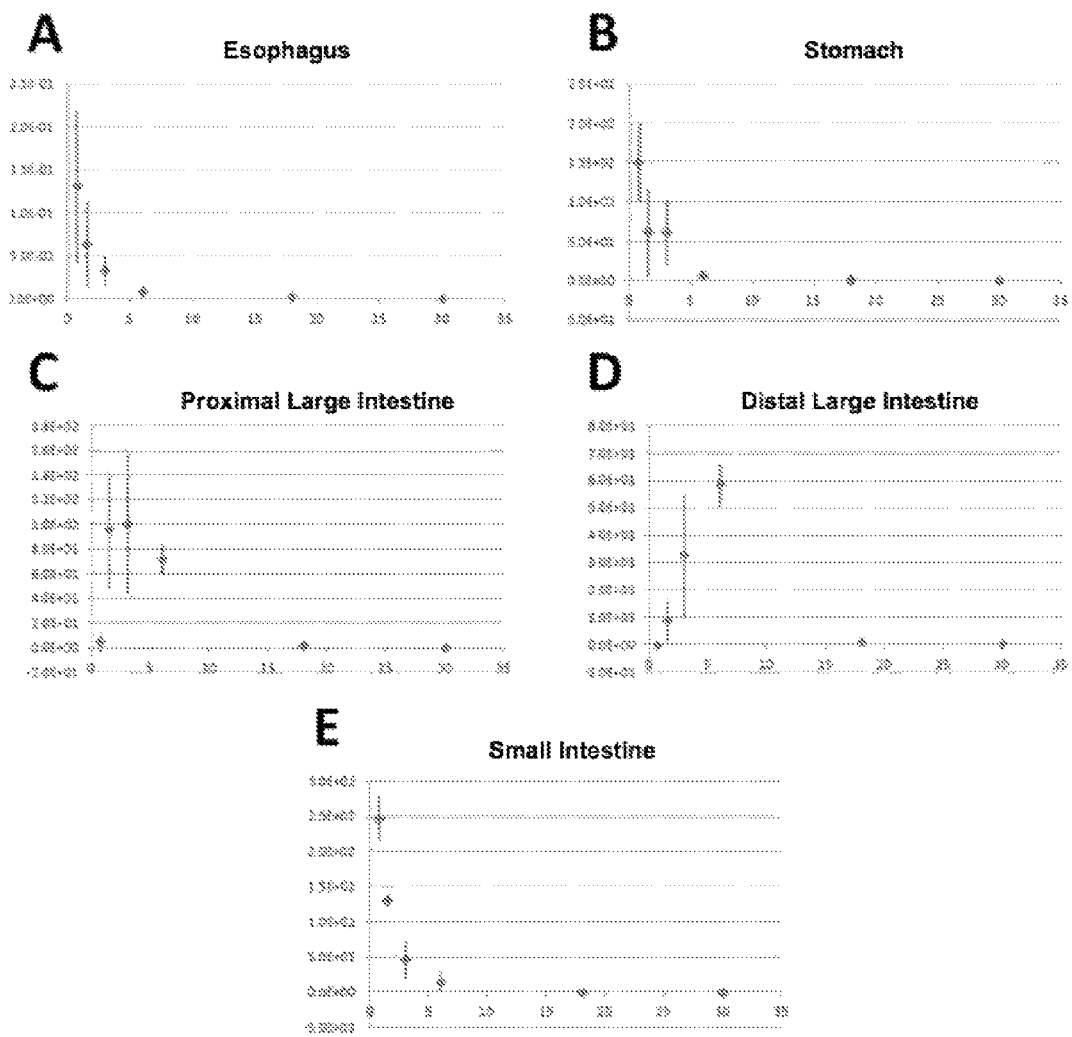

FIG. 8 shows average net activity (µCi) of radiolabeling in different organs at each time interval that mice were sacrificed. The different organs tested include (A) esophagus, (B) stomach, (C) proximal large intestine, (D) distal large intestine, and (E) small intestine. The average is represented by the bullet, and the 95% confidence interval is represented by the error bars. Because only one data point was available for some time intervals, no error bars are shown.

Figure 9:
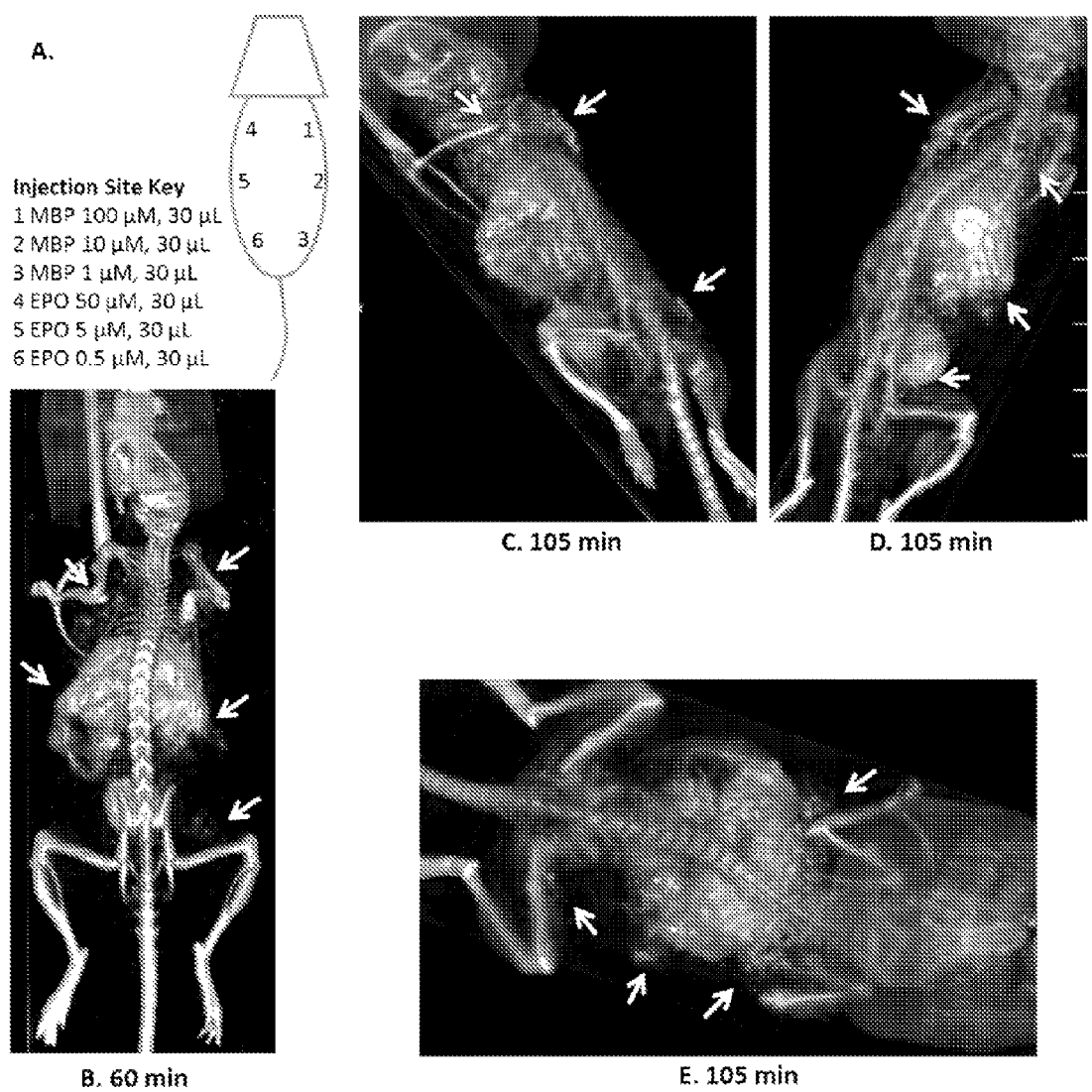

FIG. 9 shows intravenous-based localization of eosinophil granule proteins. Mice were injected subcutaneously with granule proteins MBP-1 and EPO at six sites (A), followed by tail vein administration of $^{99m}$Tc-heparin, the same conjugate used for oral administration. After 60 minutes (B), and 105 minutes (C-E), activity was apparent at the subcutaneous MBP-1/EPO injection sites (arrows). The locations of MBP-1 and EPO can be identified at relevant concentrations, with higher concentration injections accumulating more of the $^{99m}$Tc-heparin.

DETAILED DESCRIPTION

What is needed in the art are compositions and non-invasive methods for diagnosing eosinophil degranulation-associated esophagitis in a subject and for monitoring the effectiveness of treatment in the subject in order to decrease suffering and cost and to increase subject compliance. Eosinophil degranulation-associated esophagitis is eosinophilic esophagitis (EoE). The disclosed methods can diagnose eosinophilic esophagitis in a subject by detecting the presence of eosinophil granule proteins in the esophageal mucosal tissue. Thus, the diagnosis can be made even when morphologically intact eosinophils cannot be found in the inflamed tissue under microscopic examination.

Thus, disclosed is the surprising discovery that anionic heparin radiolabeled with Technetium-99m (i.e., $^{99m}$Tc or Tc-99m) can be used as a contrast agent probe to localize cationic eosinophil granule proteins, which are absent in the normal esophagus but are deposited in and are associated with inflammation in the mucosal tissue of the esophagus after eosinophil degranulation in a subject with EoE.

The present invention may be understood more readily by reference to the following detailed description of various aspects of the invention and the Examples included therein and to the Figures and their previous and following description.

Before the present compounds, compositions, articles, devices, and/or methods are disclosed and described, it is to be understood that this invention is not limited to specific synthetic methods or specific radiolabeled contrast agents, as such may, of course, vary. It is also to be understood that the terminology used herein is for the purpose of describing particular aspects only and is not intended to be limiting.

As used in the specification and the appended claims, the singular forms "a," "an," and "the" include plural referents unless the context clearly dictates otherwise. Thus, for example, reference to "a radiolabeled contrast agent" or a "radiolabeled heparin/eosinophil granule protein complex" can include mixtures of radiolabeled contrast agents or mixtures of radiolabeled heparin/eosinophil granule protein complexes, respectively, and the like.

Ranges may be expressed herein as from "about" one particular value and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant, both in relation to the other endpoint and independently of the other endpoint.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a radiolabeled contrast agent is disclosed and discussed and a number of modifications that can be made to a number of molecules including the radiolabel and contrast agent are discussed, each and every combination and permutation of the radiolabel and contrast agent and the modifications that are possible are specifically contemplated unless specifically indicated to the contrary. Thus, if a class of molecules A, B, and C is disclosed as well as a class of molecules D, E, and F and an example of a combination molecule A-D is disclosed, then even if each is not individually recited, each is individually and collectively contemplated. Thus, in this example, each of the combinations A-E, A-F, B-D, B-E, B-F, C-D, C-E, and C-F is specifically contemplated and should be considered disclosed from disclosure of A, B, and C; D, E, and F; and the example combination A-D. Likewise, any subset or combination of these is also specifically contemplated and disclosed. Thus, for example, the sub-groups of A-E, B-F, and C-E are specifically contemplated and should be considered disclosed from disclosure of A, B, and C; D, E, and F; and the example combination A-D. This concept applies to all aspects of this application including, but not limited to, steps in the methods of making and using the disclosed radiolabeled contrast agents and radiolabeled heparin/eosinophil granule protein complexes. Thus, if there are a variety of additional steps that can be performed, it is understood that each of these additional steps can be performed with any specific aspect or combination of aspects of the disclosed methods and that each such combination is specifically contemplated and should be considered disclosed.

Those skilled in the art will recognize, or be able to ascertain using no more than routine experimentation, many equivalents to the specific aspects of the methods and compositions described herein. Such equivalents are intended to be encompassed by the appended claims.

Unless defined otherwise, all technical and scientific terms used herein have the same meanings as commonly understood by one of skill in the art to which the disclosed methods and compositions belong. Although any methods and materials similar or equivalent to those described herein can be used in the practice or testing of the disclosed methods and compositions, the particularly useful methods, devices, and materials are as described.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinence of the cited documents.

It is understood that the disclosed methods and compositions are not limited to the particular methodology, protocols, and reagents described, as these may vary. It is also to be understood that the terminology used herein is for the purpose of describing particular aspects only and is not intended to limit the scope of the present invention which will be limited only by the appended claims.

In this specification and in the claims which follow, reference will be made to a number of terms which shall be defined to have the following meanings. The word "comprise" and variations of the word, such as "comprising" and "comprises," means "including, but not limited to" and is not intended to exclude, for example, other additives, components, integers or steps. "Optional" or "optionally" means that the subsequently described event or circumstance may or may not occur and that the description includes instances where said event or circumstance occurs and instances where it does not. As used herein, by "subject" is meant an individual. A subject can be a mammal such as a primate, for example, a human. The term "subject" includes domesticated animals such as cats, dogs, etc., livestock (e.g., cattle, horses, pigs, sheep, goats, etc.), and laboratory animals (e.g., mice, rabbits, rats, gerbils, guinea pigs, possums, etc.). As used herein, the terms "subject" and "patient" are interchangeable.

Disclosed are compositions and non-invasive methods for diagnosing EoE in a subject and for monitoring the course of the disease before, during, and after treatment of the disease. Thus, provided is a method of producing a medical image of an esophagus in a subject, comprising detecting an eosinophil granule protein in the mucosal tissue of the esophagus in a subject, comprising administering to a subject radiolabeled heparin under conditions wherein the radiolabeled heparin can bind to an eosinophil granule protein, and detecting a radiolabeled heparin/eosinophil granule protein complex in the mucosal tissue of the esophagus, whereby detecting the radiolabeled heparin/eosinophil granule protein complex in the mucosal tissue of the esophagus produces a medical image of the esophagus in the subject. In one aspect, the medical image can be three-dimensional. In another aspect, the medical image can be two-dimensional.

As used herein, a "mucosal tissue" is a tissue lining various cavities within the body. Examples of a mucosal tissue include, but are not limited to, mucosal tissue lining the nose, sinuses, bronchi, lungs, conjunctiva, oral cavity, tongue, esophagus, stomach, pylorus, duodenum, jejunum, ileum, ascending colon, caecum, appendix, transverse colon, descending colon, rectum, anus, urethra, and urinary bladder. A mucosal tissue comprises an epithelial surface, glandular epithelium which secretes mucus, basement membrane, and submucosa with connective tissue. Thus, a radiolabeled heparin/eosinophil granule protein complex can be detected on the epithelial surface, in the glandular epithelial tissue, on or in the basement membrane, and in the submucosal connective tissue of a mucosal tissue in a subject. In one aspect, a mucosal tissue is from the esophagus of a subject.

As used herein, an "eosinophil granule protein" is a protein that comprises the granules in eosinophils. When an eosinophil is activated, granule proteins are released from the cell into the surrounding tissue. The released granule proteins can cause pathologic allergenic inflammatory responses in the surrounding tissue, for example esophageal mucosal tissue. Examples of eosinophil granule proteins include, but are not limited to, major basic protein (MBP), major basic protein 1 (MBP-1), major basic protein 2 (MBP-2), eosinophil derived neurotoxin (EDN), eosinophil cationic protein (ECP), and eosinophil peroxidase (EPO). Other examples of eosinophil granule proteins are provided in Kita et al., Biology of Eosinophils, Chapter 19 of Immunology, which is hereby incorporated by reference for its teaching of examples of eosinophil granule proteins. In one aspect, an eosinophil granule protein can be MBP-1.

As used herein, a "radiolabel" is an isotopic composition that can be attached to a substance, for example heparin, to track the substance as it passes through a system or tissue. A non-limiting example of a radiolabeled substance is radiolabeled heparin. In one aspect, a radiolabeled heparin can be $^{99m}$Tc-heparin. Examples of other radiolabels include, but are not limited to, $^{111}$In, $^{14}$C, $^{3}$H, $^{13}$N, $^{18}$F, $^{51}$Cr, $^{125}$I, $^{133}$Xe, $^{81m}$Kr, and $^{131}$I. Other radiolabels that can be attached to a substance, for example heparin, can be found in Table 1. A radiolabel, for example, $^{99m}$Tc, can be attached to a substance, for example heparin, using commercially available reagents well known to persons of ordinary skill in the art. In one aspect, $^{99m}$Tc-heparin can be prepared as shown in Example 1 below.

TABLE 1

Commonly utilized radiolabels

| Nuclide | Physical half-life |
|---|---|
| $^{3}$H | 12.3 years |
| $^{11}$C | 20.4 minutes |
| $^{13}$N | 10 minutes |
| $^{14}$C | 5730 years |
| $^{15}$O | 2 minutes |
| $^{18}$F | 110 minutes |
| $^{32}$P | 14.3 days |
| $^{51}$Cr | 27.7 days |
| $^{52}$Fe | 8.3 hours |
| $^{57}$Co | 271 days |

TABLE 1-continued

Commonly utilized radiolabels

| Nuclide | Physical half-life |
|---|---|
| $^{58}Co$ | 71 days |
| $^{59}Fe$ | 45 days |
| $^{60}Co$ | 5.2 years |
| $^{62}Zn$ | 9.3 hours |
| $^{62}Cu$ | 9.7 minutes |
| $^{64}Cu$ | 12.7 hours |
| $^{67}Cu$ | 2.6 days |
| $^{67}Ga$ | 78.2 hours |
| $^{68}Ga$ | 68 minutes |
| $^{76}Br$ | 16 hours |
| $^{81m}Kr$ | — |
| $^{82}Rb$ | 75 seconds |
| $^{82}Sr$ | 25.5 days |
| $^{86}Y$ | 14.74 hours |
| $^{89}Zr$ | 3.27 days |
| $^{89}Sr$ | 50.6 days |
| $^{90}Sr$ | 28.5 years |
| $^{90}Y$ | 2.7 days |
| $^{99}Mo$ | 66 hours |
| $^{99m}Tc$ | 6.0 hours |
| $^{111}In$ | 2.8 days |
| $^{113}In$ | 100 minutes |
| $^{123}I$ | 13.2 hours |
| $^{124}I$ | 4.2 days |
| $^{125}I$ | 60 days |
| $^{131}I$ | 8.0 days |
| $^{133}Xe$ | 5.3 days |
| $^{137}Cs$ | 30 years |
| $^{153}Sm$ | 1.9 days |
| $^{186}Re$ | 3.8 days |
| $^{201}Tl$ | 73 hours |

In one aspect, a radiolabeled contrast agent, for example $^{99m}Tc$-heparin, can be administered to a subject orally or by intravenous injection. Oral dosing can entail ingestion similar to routine barium studies of the esophagus. A radiolabeled contrast agent can be suspended in a thickened mixture (i.e., sucralose). Examples of thickening agents include, but are not limited to, dietary starches, such as agar-agar, alginate, carrageenan, cassia gum, cellulose gum, gellan gum, guar gum, hydroxypropylcellulose, konjac gum, locust bean gum, methylcellulose, hydroxypropyl methylcellulose, microcrystalline cellulose, pectin, and xanthan gum. Other viscosifiers include honey, agave nectar, date nectar, Kuzu or Kudzu root, arrow root, corn syrup, thick juices, maple syrup, coconut oil, and palm oil.

The dwell time in the esophagus can be controlled by varying the viscosity of a contrast agent and by increasing the time interval between swallows, thereby providing more time for a contrast agent to contact and bind to an eosinophil granule protein. Further, having a subject lie down with head below feet, so that there is some reflux within the esophagus, can prolong contact between a contrast agent and the mucosal tissue of the esophagus in a subject.

A radiolabeled contrast agent can be administered to a subject in a volume from about 0.5 mL to about 1,000 mL, including all volumes in between 0.5 mL and 1,000 mL. A person of skill can determine by methods well known in the art the volume of a contrast agent to be administered to a subject based on the age, sex, weight, and overall condition of a subject. For example, in one aspect, the volume of a contrast agent administered to a subject can be from about 0.5 mL to about 5 mL. In another aspect, the volume of a contrast agent administered to a subject can be from about 5 mL to about 250 mL. In another aspect, the volume of a contrast agent administered to a subject can be from about 10 mL to about 125 mL. In another aspect, the volume of a contrast agent administered to a subject can be from about 15 mL to about 100 mL. Thus, the volume of a contrast agent that can be administered to a subject can be, for example, about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mL, and all volumes in between.

A person of ordinary skill in the art can administer to a subject a composition comprising one or more radiolabeled contrast agents to enhance the detection of eosinophil granule proteins in the mucosal tissue of the esophagus in a subject. For example, such a composition can comprise $^{99m}Tc$-heparin, $^{111}In$-heparin, or $^{14}C$-heparin, or any combination thereof. In one aspect, a radiolabeled contrast agent can be $^{99m}Tc$-heparin. Examples of radiolabeled heparin/eosinophil granule protein complexes include, but are not limited to, $^{99m}Tc$-heparin/MBP-1, $^{99m}Tc$-heparin/MBP, $^{99m}Tc$-heparin/MBP-2, $^{99m}Tc$-heparin/EDN, $^{99m}Tc$-heparin/ECP, and $^{99m}Tc$-heparin/EPO.

After administering to a subject a composition comprising radiolabeled heparin, for example $^{99m}Tc$-heparin, a person of skill can use one or more technologies and processes to detect radiolabeled heparin/eosinophil granule protein complexes in the mucosal tissue of the esophagus in a subject, where eosinophils have degranulated and caused one or more patches of inflammation, to create a medical image to map the distribution of inflammation and deposition of eosinophil granule proteins to study the anatomy and/or pathophysiology of eosinophilic esophagitis. Examples of technologies that can be used to create a medical image include, but are not limited to, single photon emission computed tomography (SPECT), positron emission (PET) scans, X-ray, conventional or computed tomography (CT), a combination of SPECT and CT, or magnetic resonance imaging (MRI). In one aspect, for example, SPECT can optionally be used in combination with MRI and/or CT scans to produce a medical image of an esophagus having patches of eosinophilic esophagitis. Fiduciary markers on the skin of a subject can also be used to position a subject so that the subject can be imaged from day to day. For example, lasers can be used to position a subject reproducibly. This permits use of multiple scans to be precisely compared. In one aspect, a medical image can be three-dimensional. In another aspect, a medical image can be two-dimensional.

Also disclosed is a method of diagnosing eosinophilic esophagitis in a subject, comprising detecting an eosinophil granule protein in the mucosal tissue of the esophagus in a subject, comprising administering to a subject radiolabeled heparin under conditions wherein the radiolabeled heparin can bind to an eosinophil granule protein, and detecting a radiolabeled heparin/eosinophil granule protein complex in the mucosal tissue of the esophagus, whereby detecting the radiolabeled heparin/eosinophil granule protein complex in the mucosal tissue of the esophagus diagnoses eosinophilic esophagitis in the subject. In one aspect, a radiolabeled heparin/eosinophil granule protein complex can be $^{99m}Tc$-heparin/MBP-1.

In one aspect, a radiolabeled contrast agent, for example $^{99m}Tc$-heparin, can be administered to a subject orally. Oral dosing can entail ingestion similar to routine barium studies of the esophagus. A radiolabeled contrast agent can be suspended in a thickened mixture (i.e., sucralose). Examples of thickening agents include, but are not limited to, dietary starches, such as agar-agar, alginate, carrageenan, cassia gum, cellulose gum, gellan gum, guar gum, hydroxypropylcellulose, konjac gum, locust bean gum, methylcellulose, hydroxypropyl methylcellulose, microcrystalline cellulose, pectin, and xanthan gum. Other viscosifiers include honey, agave nectar, date nectar, Kuzu or Kudzu root, arrow root, corn syrup, thick juices, maple syrup, coconut oil, and palm oil.

The dwell time in the esophagus can be controlled by varying the viscosity of a contrast agent and by increasing the time interval between swallows, thereby providing more time for a contrast agent to contact and bind to an eosinophil granule protein. Further, having a subject lie down with head below feet, so that there is some reflux within the esophagus, can prolong contact between a contrast agent and the mucosal tissue of the esophagus in a subject.

A radiolabeled contrast agent can be administered to a subject in a volume from about 0.5 mL to about 1,000 mL, including all volumes in between 0.5 mL and 1,000 mL. A person of skill can determine by methods well known in the art the volume of a contrast agent to be administered to a subject based on the age, sex, weight, and overall condition of a subject. For example, in one aspect, the volume of a contrast agent administered to a subject can be from about 0.5 mL to about 5 mL. In another aspect, the volume of a contrast agent administered to a subject can be from about 5 mL to about 250 mL. In another aspect, the volume of a contrast agent administered to a subject can be from about 10 mL to about 125 mL. In another aspect, the volume of a contrast agent administered to a subject can be from about 15 mL to about 100 mL. Thus, the volume of a contrast agent that can be administered to a subject can be, for example, about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mL, and all volumes in between.

A person of ordinary skill in the art can administer to a subject a composition comprising one or more radiolabeled contrast agents to enhance the detection of eosinophil granule proteins in the mucosal tissue of the esophagus in a subject. For example, such a composition can comprise $^{99m}$Tc-heparin, $^{111}$In-heparin, or $^{14}$C-heparin, or any combination thereof. In one aspect, a radiolabeled contrast agent can be $^{99m}$Tc-heparin. Examples of radiolabeled heparin/eosinophil granule protein complexes include, but are not limited to, $^{99m}$Tc-heparin/MBP-1, $^{99m}$Tc-heparin/MBP, $^{99m}$Tc-heparin/MBP-2, $^{99m}$Tc-heparin/EDN, $^{99m}$Tc-heparin/ECP, and $^{99m}$Tc-heparin/EPO.

After administering to a subject a composition comprising radiolabeled heparin, for example $^{99m}$Tc-heparin, a person of skill can use one or more technologies and processes to detect radiolabeled heparin/eosinophil granule protein complexes in the mucosal tissue of the esophagus in a subject, where eosinophils have degranulated and caused one or more patches of inflammation, to create a medical image to map the distribution of inflammation and deposition of eosinophil granule proteins to study the anatomy and/or pathophysiology of eosinophilic esophagitis. Examples of technologies that can be used to create a medical image include, but are not limited to, single photon emission computed tomography (SPECT), positron emission (PET) scans, X-ray, conventional or computed tomography (CT), a combination of SPECT and CT, or magnetic resonance imaging (MRI). In one aspect, for example, SPECT can optionally be used in combination with MRI and/or CT scans to produce a medical image of an esophagus having patches of eosinophilic esophagitis. Fiduciary markers on the skin of a subject can also be used to position a subject so that the subject can be imaged from day to day. For example, lasers can be used to position a subject reproducibly. This permits use of multiple scans to be precisely compared. In one aspect, a medical image can be three-dimensional. In another aspect, a medical image can be two-dimensional.

Further disclosed is a method of detecting a change in eosinophilic esophagitis in a subject diagnosed with eosinophilic esophagitis, comprising: (a) producing a first medical image of the esophagus in a subject diagnosed with eosinophilic esophagitis according to the disclosed methods, (b) producing a second medical image of the esophagus in the subject of step (a) according to the disclosed methods, and (c) comparing the medical image of step (b) with the medical image of step (a), whereby detecting a change in the medical image of step (b) compared to the medical image of step (a) detects a change in eosinophilic esophagitis in the subject. In one aspect, the medical image can be three-dimensional. In another aspect, the medical image can be two-dimensional.

Thus, a person of skill can produce a first medical image of the esophagus in a subject diagnosed with EoE to have as a baseline for future comparison with later-produced medical images of the esophagus in the subject to determine what the natural history of EoE is. Further, a first medical image can be used to determine whether a treatment of EoE is effective in the subject. For example, if a second medical image is produced after the initiation of treatment of EoE in a subject and the second medical image shows fewer areas of radiolabeled heparin/eosinophil granule protein complexes (i.e., inflammation) when compared to the first medical image produced before initiation of treatment, a person of skill, for example a physician, can determine that the treatment of EoE in the subject is effective. Conversely, if a second medical image is produced after the initiation of treatment of EoE in a subject and the second medical image shows the same or more areas of radiolabeled heparin/eosinophil granule protein complexes (i.e., inflammation) when compared to the first medical image produced before initiation of treatment, a person of skill, for example a physician, can determine that the treatment of EoE in the subject is not effective.

In another aspect, disclosed is a method of detecting eosinophil degranulation in a subject, comprising detecting an eosinophil granule protein in a subject, comprising administering to a subject radiolabeled heparin under conditions wherein the radiolabeled heparin can bind to an eosinophil granule protein, and detecting a radiolabeled heparin/eosinophil granule protein complex, whereby detecting the radiolabeled heparin/eosinophil granule protein complex detects eosinophil degranulation in the subject.

In one aspect, a radiolabeled contrast agent, for example $^{99m}$Tc-heparin, can be administered to a subject orally or intravenously. Oral dosing can entail ingestion similar to routine barium studies of the esophagus. A radiolabeled contrast agent can be suspended in a thickened mixture (i.e., sucralose). Examples of thickening agents include, but are not limited to, dietary starches, such as agar-agar, alginate, carrageenan, cassia gum, cellulose gum, gellan gum, guar gum, hydroxypropylcellulose, konjac gum, locust bean gum, methylcellulose, hydroxypropyl methylcellulose, microcrystalline cellulose, pectin, and xanthan gum. Other viscosifiers include honey, agave nectar, date nectar, Kuzu or Kudzu root, arrow root, corn syrup, thick juices, maple syrup, coconut oil, and palm oil.

The dwell time in the esophagus can be controlled by varying the viscosity of a contrast agent and by increasing the time interval between swallows, thereby providing more time for a contrast agent to contact and bind to an eosinophil granule protein. Further, having a subject lie down with head below feet, so that there is some reflux within the esophagus, can prolong contact between a contrast agent and the mucosal tissue of the esophagus in a subject.

A radiolabeled contrast agent can be administered to a subject in a volume from about 0.5 mL to about 1,000 mL, including all volumes in between 0.5 mL and 1,000 mL. A person of skill can determine by methods well known in the art the volume of a contrast agent to be administered to a subject based on the age, sex, weight, and overall condition of a subject. For example, in one aspect, the volume of a contrast agent administered to a subject can be from about 0.5 mL to about 5 mL. In another aspect, the volume of a contrast agent administered to a subject can be from about 5 mL to about 250 mL. In another aspect, the volume of a contrast agent administered to a subject can be from about 10 mL to about 125 mL. In another aspect, the volume of a contrast agent administered to a subject can be from about 15 mL to about 100 mL. Thus, the volume of a contrast agent that can be administered to a subject can be, for example, about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mL, and all volumes in between.

A person of ordinary skill in the art can administer to a subject a composition comprising one or more radiolabeled contrast agents to enhance the detection of eosinophil granule proteins in the mucosal tissue of the esophagus in a subject. For example, such a composition can comprise $^{99m}$Tc-heparin, $^{111}$In-heparin, or $^{14}$C-heparin, or any combination thereof. In one aspect, a radiolabeled contrast agent can be $^{99m}$Tc-heparin. Examples of radiolabeled heparin/eosinophil granule protein complexes include, but are not limited to, $^{99m}$Tc-heparin/MBP-1, $^{99m}$Tc-heparin/MBP, $^{99m}$Tc-heparin/MBP-2, $^{99m}$Tc-heparin/EDN, $^{99m}$Tc-heparin/ECP, and $^{99m}$Tc-heparin/EPO.

After administering to a subject a composition comprising radiolabeled heparin, for example $^{99m}$Tc-heparin, a person of skill can use one or more technologies and processes to detect radiolabeled heparin/eosinophil granule protein complexes in the mucosal tissue of the esophagus in a subject, where eosinophils have degranulated and caused one or more patches of inflammation, to create a medical image to map the distribution of inflammation and deposition of eosinophil granule proteins to study the anatomy and/or pathophysiology of eosinophilic esophagitis. Examples of technologies that can be used to create a medical image include, but are not limited to, single photon emission computed tomography (SPECT), positron emission (PET) scans, X-ray, conventional or computed tomography (CT), a combination of SPECT and CT, or magnetic resonance imaging (MRI). In one aspect, for example, SPECT can optionally be used in combination with MRI and/or CT scans to produce a medical image of an esophagus having patches of eosinophilic esophagitis. Fiduciary markers on the skin of a subject can also be used to position a subject so that the subject can be imaged from day to day. For example, lasers can be used to position a subject reproducibly. This permits use of multiple scans to be precisely compared. In one aspect, a medical image can be three-dimensional. In another aspect, a medical image can be two-dimensional.

EXAMPLES

The following examples are put forth so as to provide those of ordinary skill in the art with a complete disclosure and description of how the compounds, compositions, articles, devices and/or methods claimed herein are made and evaluated and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight; temperature is in ° C. or is at ambient temperature; and pressure is at or near atmospheric.

Example 1 Preparation of $^{99m}$Tc-Heparin

Figure 3:
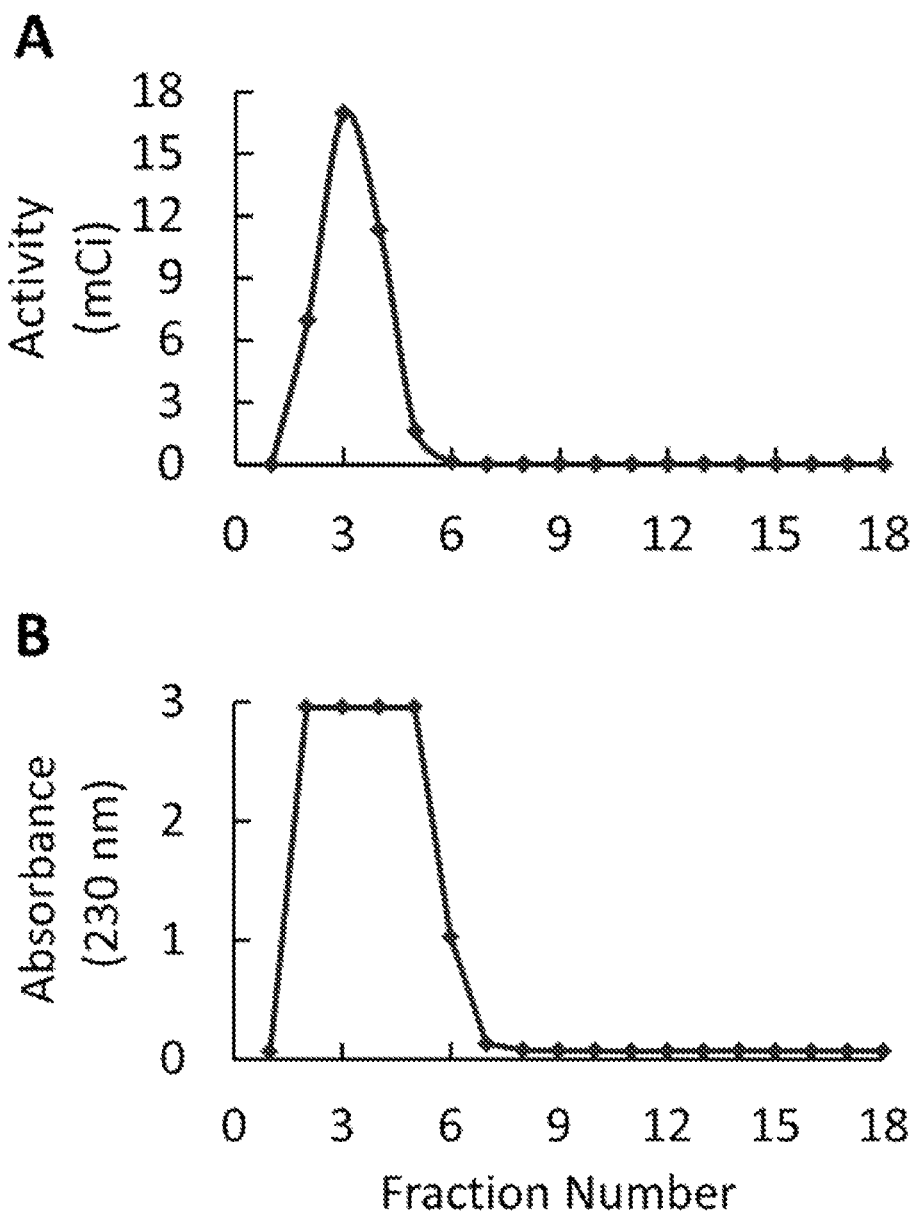
FIG. 3 shows $^{99m}$Tc-heparin binding affinity. Samples were prepared using 100 mCi of $^{99m}$Tc fresh tin solution heparin (150 mg). Samples were run through a Hi-trap G25 desalting column, and paper confirmed >97% binding. (A) Shows the radiolabel activity of each collected chromatography fraction, which consisted of 30 drops and constituted roughly 1 mL. (B) Shows absorbance of each fraction at 230 nm. There were no second peaks of unbound $^{99m}$Tc, and the activity peak correlates with the absorbance peak.

Solutions of stannous chloride (40 mg/mL, Sigma 243523) were prepared in deionized water under flowing nitrogen. A 0.5 mL aliquot was filtered and mixed with 1.00 mL NaCl (1.00 M) plus 150 mg of preservative-free heparin (10,000 IU/mL). Approximately 100 mCi of freshly eluted $^{99m}$Tc was added and mixed for 30 minutes at room temperature. Aliquots containing approximately 10 mCi of $^{99m}$Tc and 20 mg of heparin were removed for tissue experiments. FIG. 3A shows the labeling affinity, measured by paper chromatography Whatman number 31 with acetone, showed more than 97% binding of heparin to $^{99m}$Tc. Radiolabeled heparin was also analyzed by Sephadex G25 column chromatography (HiTrap 5 mL desalting columns, GE healthcare, 17140801) with 0.15 M NaCl as the elution buffer, and approximately 1 mL fractions were collected. FIG. 3B shows radioactivity eluted at fraction 4 (free $^{99m}$Tc elutes at fraction 13), demonstrating that all of the $^{99m}$Tc eluted at the void volume and confirming that there is no unbound $^{99m}$Tc in the radiolabeled heparin. The stability of $^{99m}$Tc-heparin in an acidic environment was tested by diluting in artificial gastric juice (Carolina, 864603) and showing that its properties were unaltered, using both paper chromatography and Sephadex G25.

Example 2 Esophageal Biopsies

Esophageal biopsies were collected from a prior elemental diet study (IRB 00040035 University of Utah) and kept frozen at −70° C. Biopsies from each patient were selected for histological analysis for eosinophil density or radiolabeling. Biopsies from EoE patients who resolved their eosinophilia under the elemental diet were chosen as negative controls. Tissues from resolved EoE and active EoE patients were incubated with the $^{99m}$Tc-heparin, washed in buffered saline, and imaged using SPECT.

Example 3 Analysis of Radiolabeled Biopsies

The activity of radiolabeled biopsy tissues was measured using dose calibrators (Capintec model CRC-15R). Two-dimensional planar static images of the radiolabeled biopsies were obtained using the Ecam SPECT instrument (Siemens). The images were acquired for 3 minutes each using a 1.0 magnification, 256 by 256 matrix size. Correlation between eosinophil densities and SPECT counts obtained by 2D imaging were evaluated by Spearman rank correlation analysis.

Figure 1:
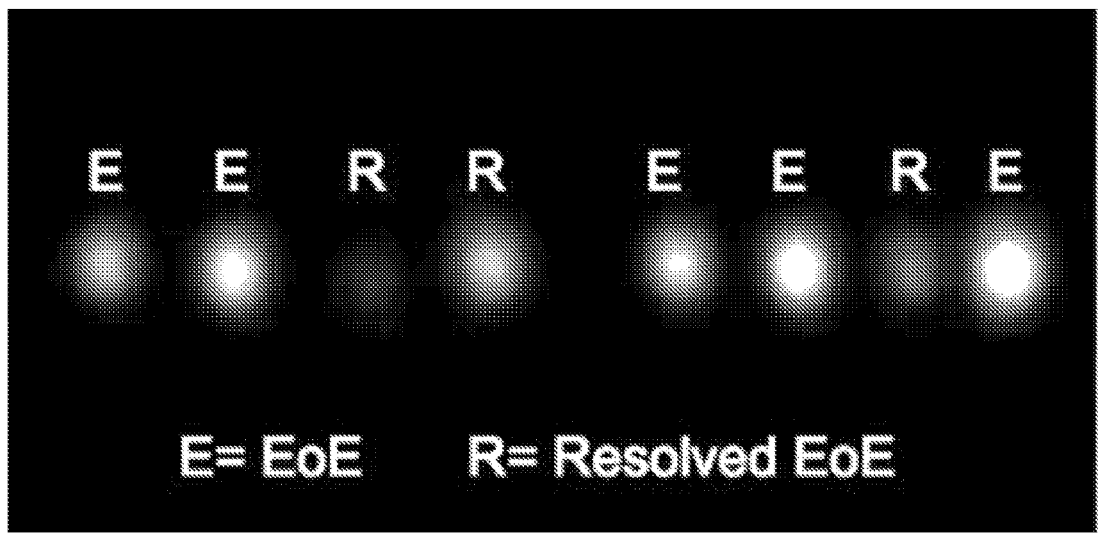
FIG. 1 shows a 2D planar SPECT image of biopsies from active EoE (>15 eosinophils (eos) per high power field (hpf) of view) and resolved EoE patients (<15 eos/hpf) after being incubated with $^{99m}$Tc-heparin.
Figure 2:
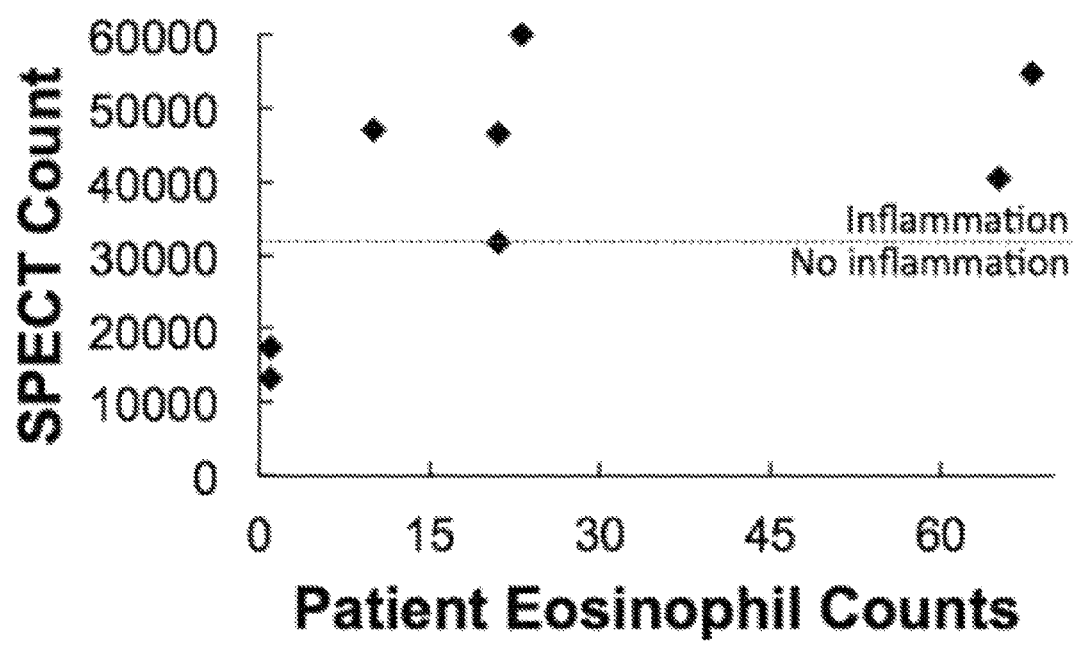
FIG. 2 shows SPECT count of biopsies as a function of eosinophil counts from the same patients as shown in FIG. 1.

Table 2 presents the SPECT counts of each biopsy, summarizing its radioactivity and eosinophil density. Histopathological analyses confirmed that only samples 1-5 had greater than 15 eosinophils/hpf. FIGS. 1 and 2 show that active EoE cases can be differentiated from resolved EoE cases using this technique. The Spearman rank correlation analysis found a monotonic correlation between eosinophil density and SPECT count with a p value less than 0.05. Even though the eosinophil densities were not derived from identical biopsy tissues used for SPECT imaging, tissues from inflamed patients displayed significant binding to $^{99m}$Tc-heparin that correlates with eosinophil density.

TABLE 2

Radioactivity measurements, histological data, and the SPECT count of EoE versus control samples

| Sample Number | Disease Criteria | Eosinophil Density/hpf | Activity µCi | SPECT Count |
|---|---|---|---|---|
| 1 | Active EoE | 68 | 180 | 59634 |
| 2 | Active EoE | 65 | 128 | 40474 |
| 3 | Active EoE | 21 | 101 | 46457 |
| 4 | Active EoE | 23 | 131 | 59923 |
| 5 | Active EoE | 21 | 70 | 31780 |
| 6 | Resolved EoE | 10 | 147 | 47048 |
| 7 | Resolved EoE | 1 | 29.3 | 13202 |
| 8 | Resolved EoE | 1 | 37 | 17518 |

Example 4 Quality Control of Radiolabeled Heparin

Thin layer chromatography (TLC) can be performed on Whatman 31ET strips with acetone as the solvent. A chromatography chamber can be prepared by adding just enough acetone solvent so that it covers the bottom of the chromatography chamber. A small sample of $^{99m}$Tc-heparin can be placed at 1 cm from the bottom of the strip. This is the origin. A spotted SG strip can be placed into the chromatography chamber making sure that the origin of the sample is not immersed in the solvent. When the solvent reaches the top of the strip, the solvent front, the strip can be removed from the chromatography chamber. The strip can be cut in half between the origin and solvent front. Each strip can be counted using the Ludlum 2200 scaler/ratemeter attached to a 1"×1" sodium iodide detector. Each strip can be counted for 1 minute (cpm). A background (bkg) count can be obtained before counting each strip. The background count can be subtracted from each count. The radiochemical purity for $^{99m}$Tc-heparin can be calculated using the following formula:

Background cpm (bkg), Origin cpm, and Solvent Front cpm are measured.

$$\text{Percentage }^{99m}Tc\text{-heparin} = \frac{(\text{Origin } cpm - bkg\ cpm)}{(\text{Origin } cpm - bkg\ cpm) + (\text{Solvent Front } cpm - bkg\ cpm)}$$

The final product can be clear and free of particulate matter. The radiochemical purity for $^{99m}$Tc-heparin can be >90%.

Example 5 Alternative Preparation of $^{99m}$Tc-Heparin $^{99m}$Tc-heparin was prepared by diluting stannous chloride (5 mg/mL, Sigma 243523) in water under flowing nitrogen. A 0.10 mL aliquot was filtered and mixed with 15 mg of preservative free heparin (10,000 IU/mL). Approximately 5 mCi of freshly eluted $^{99m}$Tc was added and mixed in for 15 minutes at room temperature. Hundred microliter aliquots containing approximately 0.5 mCi of $^{99m}$Tc and 1.5 mg of heparin were removed for oral administration to mice. Quality control was determined by paper chromatography (Whatman no. 31) with acetone.

Example 6 Quantitative Organ Biodistribution

All animal experiments were performed in accordance with approved University of Utah Institutional Animal Care and Use Committee (IACUC) protocols. $^{99m}$Tc-heparin (approximately 0.5 mCi/mouse, 15 mg) was administered directly to the stomach of healthy adult mice (C57Bl/6, Charles River Laboratories International, Inc., average weight=29.14±1.5 g) by oral gavage under brief restraint using a straight 1.5 in., 20-gauge needle with a 1.25 mm ball tip. Three animals per group were euthanized with $CO_2$ at 45 minutes, 1.5, 3, 6, 18, and 30 hours. With care to avoid cross-contamination, whole organs, blood, and hind leg muscle samples were harvested within approximately 20 min, weighed, and counted for up to 2 min in captus 3000 well counter (Bicorn model 2MW2/2-X NaI drilled well crystal detector in a Canberra 727 well). The proximal large intestine was considered to include the caecum plus ¾ in distal small intestine, while the remainder was considered distal large intestine. Larynx and thyroid were harvested and measured together. No gastrointestinal pelvic samples included reproductive organs and surrounding fatty tissue. Results are expressed as the percentage injected dose per gram of harvested organ (% ID/g).

The biodistribution of $^{99m}$Tc-heparin acquired at time of harvest as measured by well counting is shown in FIG. 6. Forty-five minutes after oral administration, the stomach and small intestine were the major organs of $^{99m}$Tc-heparin accumulation. The proximal large intestine showed the highest uptake at 1.5 h after oral administration. The majority of activity after 6 h incubation of $^{99m}$Tc-heparin was in distal large intestine. Little uptake was observed in esophagus, lung and thyroid. The very modest uptake in the esophagus may be due to esophageal reflux associated with the oral gavage. All other organs showed negligible uptake in all the time points, indicating that $^{99m}$Tc-heparin is not absorbed significantly outside of the GI tract.

Example 7 SPECT Imaging

To obtain qualitative images of $^{99m}$Tc activity, mice were anesthetized with isoflurane gas (5% induction, 1-2% maintenance, IMWI/VetOne, Meridian, Id., Cat #501017) and positioned prone on the scanner bed 40 min prior to euthanasia time. SPECT/CT images of mice were acquired by using an INVEON™ trimodality PET/SPECT/CT scanner (Siemens Preclinical Solutions, Knoxville, Tenn.). A sensor (Biovet, France) was used to monitor the respiration rate of mice under anesthesia. CT images consisting of 220 degrees and 480 projections at each of 2 bed positions were acquired first. The exposure time was 135 ms with a detector setting at 80 peak kilovoltage (kVp) and 500 µA. Data were reconstructed onto a 416×416×752 image matrix using the COBRA software package (Exxim Computing Corporation, Pleasanton, Calif.). The effective image pixel size was 97 µm. SPECT data were acquired immediately following the CT using a 2 mm single pinhole collimator with a detector radius of rotation at 35 mm. Images were acquired over 1.5 detector revolutions with 6° between each of 90 projections. A 90 mm bed travel was used. Each projection was acquired for 12 seconds, and the data were histogrammed with a 10% window centered at 140 keV. Reconstruction was performed using ordered subset expectation maximization 3D (OSEM3D) with 8 iterations and 6 subsets. Reconstructed images were analyzed and visualized using the Siemens INVEON™ Research Workplace (IRW) software.

To visually track the radiolabeled dose in mice, qualitative images of $^{99m}$Tc activity were obtained with SPECT/CT. SPECT/CT images of mice were acquired at 3, 6, 18, and 30 hours after oral administration. FIG. 7 shows the activity mostly in the GI tract, i.e., stomach and intestines. No localization was visualized in liver, kidney, or lung, indicating that $^{99m}$Tc-heparin was not absorbed through the GI tract and was not circulating in the blood.

Example 8 Radiation Dose Calculation for Orally Administered $^{99m}$Tc-Heparin

The OLINDA/EXM dose estimation software was used to determine the effective doses and doses to individual organs on calculations and constants defined in the ICRP Publication 106. This software includes a kinetic input module with exponential curve fitting of the input data for determining the number of disintegrations per unit of administered activity (µCi-h/µCi) in each source organ. Residence times in the various organs were measured using trapezoidal averaging of the averaged data for each time interval.

Radiation dose calculations were performed based on the data obtained from mice administered $^{99m}$Tc-heparin by oral gavage. The data were obtained from 18 mice sacrificed at six time intervals, with a total of three data points at each time interval. Dose calculations were performed based on the simple average of the three data points at each time interval. The 95% confidence interval was calculated based on these data points.

Good recovery of the $^{99m}$Tc-heparin was observed. Between 89 and 99% of the administered material and 99% of the material measured just prior to sacrifice was recovered.

Residence times in the various organs were measured using trapezoidal averaging of the averaged data for each time interval. A simple average of the data was used.

Mouse to human estimate was performed through simple mass weighting techniques. Human data were based on ICRP 106 values. Mouse data were measured for each mouse and individual organ. Simple averages of mouse-to-human estimates were used.

Data were collected for 22 different organs. However, over 98% of the accumulated activity was observed in the GI tract. FIG. 8 shows the average net activity (µCi) at each time interval. The uptake by the proximal and distal intestine gradually increased over 3 and 6 hours, respectively, and then decreased until 30 hours. Little radioactivity level was observed in esophagus, lung and thyroid, and negligible activity was observed elsewhere.

Using the average accumulated activities (scaled for mouse-to-human estimate), the average dose to individual organs was calculated. Table 3 shows the results of the estimated dose to a human from orally administered $^{99m}$Tc-heprin. These results are listed in descending order based on the dose to the organ. Note that greater than 98% of the organ dose is to the organs of the GI tract.

TABLE 3

Dose to individual organ from orally administered $^{99m}$Tc-heparin, human corrected
Human corrected

| Organ | A (µCi-hr/µCi) | Fraction of Total |
| --- | --- | --- |
| Dist. Lg. Int | 4.355E−01 | 2.916E−01 |
| Small Int. | 4.226E−01 | 2.829E−01 |
| Prox. Lg. Int. | 3.602E−01 | 2.411E−01 |
| Stomach | 2.541E−01 | 1.701E−01 |
| Lung | 2.012E−02 | 1.347E−02 |
| Urine | 3.830E−04 | 2.564E−04 |
| Liver | 2.708E−04 | 1.813E−04 |
| Esophagus | 2.359E−04 | 1.579E−04 |
| Larynx/Thyroid | 1.381E−04 | 9.248E−05 |
| Bladder | 9.002E−05 | 6.026E−05 |
| Kidney | 7.918E−05 | 5.300E−05 |
| Heart | 4.281E−05 | 2.866E−05 |
| Trachea | 3.724E−05 | 2.493E−05 |
| Pancreas | 2.300E−05 | 1.540E−05 |
| Spleen | 1.452E−05 | 9.719E−06 |
| Testicles | 1.206E−06 | 8.072E−07 |
| Thymus | 6.022E−07 | 4.032E−07 |
| Gall Bladder | 5.582E−07 | 3.737E−07 |

Having estimated residence times and organ doses, the effective dose was estimated. In order to estimate effective dose, OLINDA/EXM dose estimation software was used. OLINDA is an FDA approved software tool for dose estimation and has received 501(k) approval. The estimated residence times were input into OLIDNA. The results for adults are shown in Table 4. Note that approximately 74% of the contribution to the effective dose is from the organs in the GI tract. The dose contribution from the ovaries and bone marrow was a result of the accumulated activity in other organs (i.e., irradiation from accumulated activity in surrounding organs). Accumulated activity in these organs was not specifically determined

TABLE 4

OLINDA results for Adults using estimated residence times

| | mGy/MBq | Fraction of Total Dose |
| --- | --- | --- |
| LLI Wall | 2.46E−03 | 5.12E−01 |
| Stomach Wall | 1.04E−03 | 2.17E−01 |
| Ovaries | 8.87E−04 | 1.85E−01 |
| Red Marrow | 1.02E−04 | 2.12E−02 |
| ULI Wall | 6.83E−05 | 1.42E−02 |
| Urinary Bladder Wall | 6.64E−05 | 1.38E−02 |
| Lungs | 4.92E−05 | 1.02E−02 |
| Small Intestine | 4.68E−05 | 9.75E−03 |
| Liver | 2.99E−05 | 6.23E−03 |
| Uterus | 1.32E−05 | 2.75E−03 |
| Pancreas | 8.27E−06 | 1.72E−03 |
| Osteogenic Cells | 7.83E−06 | 1.63E−03 |
| Spleen | 5.61E−06 | 1.17E−03 |
| Kidneys | 4.84E−06 | 1.01E−03 |
| Breasts | 4.73E−06 | 9.85E−04 |
| Muscle | 3.00E−06 | 6.25E−04 |
| Adrenals | 2.70E−06 | 5.62E−04 |
| Skin | 1.77E−06 | 3.69E−04 |
| Thyroid | 5.46E−07 | 1.14E−04 |
| Thymus | 3.60E−07 | 7.50E−05 |
| Brain | 5.45E−09 | 1.13E−06 |
| Gallbladder Wall | 0.00E+00 | 0.00E+00 |

TABLE 4-continued

OLINDA results for Adults using estimated residence times

|  | mGy/MBq | Fraction of Total Dose |
|---|---|---|
| Heart Wall | 0.00E+00 | 0.00E+00 |
| Testes | 0.00E+00 | 0.00E+00 |
| Effective Dose (mSv/MBq) | 4.81E−03 | |

Example 9 Patient Administration

A patient may not eat or drink anything except water after midnight the night before the scan. An oral dose of about 10 mCi $^{99m}$Tc-heparin can be administered to the patient.

2D planar images can be acquired over time during the swallowing process. Additional 2D planar body images can be taken and used to determine the relative biodistribution of $^{99m}$Tc-heparin. A 3D SPECT image can be acquired. The patient can be re-imaged after drinking water.

Upon completion of the study, the patient can be removed from the scanner and encouraged to void. The patient can be instructed to drink plenty of fluids and void frequently throughout the day to help reduce radiation exposure.

Example 10 Monkey Esophagus Tissue Experiment

Monkey esophagus biopsy samples were incubated with MBP-1 (treated sample) overnight. Samples incubated with PBS were used as a negative control. Radiolabeled binding of $^{99m}$Tc-heparin was examined as a function of washing steps with PBS, time, and heparin molarity. Results of binding experiments are shown in FIG. 4. FIG. 5 shows a representative SPECT image of monkey esophagus biopsy tissue after incubation with $^{99m}$Tc-heparin. Higher SPECT intensity of $^{99m}$Tc-heparin is clearly visible in the MBP-1 treated sample compared to the control.

Example 11 Co-Localization of $^{99m}$Tc-Heparin Activity with Eosinophil Granule Protein Injection Sites In order to demonstrate in vivo targeting and intravenous administration of the radiocontrast agent $^{99m}$Tc-heparin, eosinophil granule proteins MBP-1 and EPO were injected subcutaneously into healthy, anesthetized C57BL6 mice to simulate local eosinophilia, as a positive control. $^{99m}$Tc-heparin was administered intravenously via tail vein after the injection of the eosinophil granule proteins and was given time to bind the eosinophil granule proteins. FIG. 9A depicts the sites and concentrations of the subcutaneously injected eosinophil granule proteins. The mice were imaged using an Inveon trimodality scanner (Siemens Preclinical Solutions, Knoxville, Tenn.). SPECT/CT Scans were completed at 60 and 105 minutes after intravenous administration of $^{99m}$Tc-heparin.

SPECT/CT images depicting the distribution of $^{99m}$Tc-heparin are shown in FIG. 9 (B-E). The $^{99m}$Tc-heparin spread throughout the major blood organs, particularly the liver, spleen, and kidneys, as well as the bladder. However, there was additional activity at the injection sites (arrows) not present in negative control mice that had not been injected with eosinophil granule proteins, indicating successful co-localization of $^{99m}$Tc-heparin with the eosinophil granule proteins. Activity was clearly visible and correlated with the concentration of MBP-1 at the injection sites. Only the highest concentration EPO site clearly showed significant $^{99m}$Tc-heparin presence. Observations at necropsy revealed no significant hemorrhage to confound the positive result.

REFERENCES

Abu-Ghazaleh R I, et al., "Eosinophil granule proteins in peripheral blood granulocytes," *J Leukoc Biol* 1992, 52: 611-618.

Attwood S E, et al., "Esophageal eosinophilia with dysphagia. A distinct clinicopathologic syndrome," *Dig Dis Sci* 1993, 38(1): 109-116.

Esquerre J P, et al., "Kinetics of technetium-labeled heparin in thromboembolism: Preliminary Report," *Int. J Nucl. Med. Biol.,* 1979: 6 (4):215-220.

Fogg M I, et al., "Pollen and eosinophilic esophagitis," *J Allergy Cin Immunol* 2003, 112(4): 796-797.

Frigas E, et al., "Cytotoxic effects of the guinea pig eosinophil major basic protein on tracheal epithelium," *Lab Invest* 1980, 42: 35-43.

Gangotena F, et al., "Eosinophilic Esophagitis, Ringed Esophagus: The Diagnostic Conundrum," *Am J Gastroenterol* 2007, 102: S145-S146, Abstract 79.

Gleich G J et al., "Biochemical and functional similarities between human eosinophil-derived neurotoxin and eosinophil cationic protein: homology with ribonuclease," *Proc Natl Acad Sci USA* May, 1986, 83: 3146-3150.

Gleich G J et al., "Comparative properties of the Charcot-Leyden crystal protein and the major basic protein from human eosinophils," *J Clin Invest March,* 1976, 57: 633-640.

Gleich, G J et al., "Physiochemical and biological properties of the major basic protein from guinea pig eosinophil granules," *J Exp Med* 1974, 140: 313-332.

Gonsalves N et al., "A Prospective Trial of Six Food Elimination Diet and Reintroduction of Causative Agents in Adults with Eosinophilic Esophagitis," *Digestive Disease Week Presentation* 2008, Abstract No. 727.

Gonsalves N et al., "Histopathologic variability and Endoscopic Correlates in Adults with Eosinophilic Esophagitis," *Gastrointestinal Endosc* 2006, 64(3): 313-319.

Gonsalves N et al., "Prospective Clinical Trial of Six Food Elimination Diet or Elemental Diet in the Treatment of Adults with Eosinophilic Gastroenteritis," *Digestive Disease Week Presentation* 2009, Abstract No. S1861.

Gonsalves N, Kahrilas P, "Eosinophilic Esophagitis in Adults," *Am J Gastroenterol Clin N Am* 2008, 37: 349-368.

Gundel R H et al., "Human eosinophil major basic protein induces airway constriction and airway hyperresponsiveness in primates," *J Clin Invest,* 1991, 87: 1470-1473.

Hiebert L M, et al., "Tissue distribution and antithrombotic activity of unlabeled or C14-labeled porcine intestinal mucosal heparin following administration to rats by the oral route," *Can J Physiol Pharmacol.,* 2000; 78: 307-320.

Hirash J, et al., "Heparin and low-molecular-weight heparin: mechanisms of action, pharmacokinetics, dosing, monitoring, efficacy, and safety," *Chest.* 2001, 119: 64S-94S.

ICRP, 2008. Radiation Dose to Patients from Radiopharmaceuticals—Addendum 3 to ICRP Publication 53. *ICRP Publication* 106. Ann. ICRP 38 (1-2).

Kagawalla A F et al., "Effect of 6 food Elimination diet on clinical and histologic outcomes in eosinophilic esophagitis," *Clin Gastroenterol Hepatol* 2006, 4: 1097-1102.

Kato M et al., "Eosinophil infiltration and degranulation in normal human tissue," *Anat Record* 1998, 252: 418-425.

Kephart G M et al., "Marked deposition of eosinophil-derived neurotoxin in adult patients with eosinophilic esophagitis," *Am J Gastroenterol* 2010, 105(2): 298-307.

Konikoff et al., "A Randomized, Double-blind, Placebo controlled trial of Fluticasone Propionate for Pediatric Eosinophilic Esophagitis," *Gastroenterol* 2006, 131: 1381-1391.

Kulkarni P V, et al., "Technetium Labeled Heparin: Preliminary Report of a New Radiopharmaceutical with Potential for Imaging Damaged Coronary Arteries and Myocardium," *J Nucl Med* 1978, 19: 810-815.

Kulkarni P V, et al., "Modified technetium-99m heparin for the imaging of acute experimental myocardial infarcts," *J Nucl Med.* 1980, 21: 117-121.

Laforest M D, et al., "Pharmacokinetics and biodistribution of technetium 99m labelled standard heparin and a low molecular weight heparin (enoxaparin) after intravenous injection in normal volunteers," *Br J Haematol.* 1991, 77: 201-208.

Levine et al., "Disease of the Esophagus: Diagnosis with Esophagography," *Radiology* 2005, 237: 414-427.

Liacouras C A et al., "Eosinophilic Esophagitis: a 10-year experience in 381 children," *Clin Gastroenterol hepatol* 2005, 3: 1198-1206.

Liacouras C, et al., "Eosinophilic Esophagitis: Updated Consensus Recommendations for children and adults," *J Allergy Clin Immunol.* 2011, 128(1): 3-20.

Mackenzie S et al., "Eosinophilic Oesophagitis in Patients Presenting with Dysphagia—A Prospective Analysis," *Aliment Pharmacol Therapeutics* 2008, 28(9): 1140-1146.

Majdalani G, et al., "Kinetics of technetium-labeled heparin in hemodialyzed patients," *Kidney Int. Supply.*, 1993:41: S131-134.

Markowitz J et al., "Elemental Diet is Effective Treatment for Eosinophilic Esophagitis in Children and Adolescents," *Am J Gastroenterol* 2003, 98: 777-782.

Mishra A et al., "An etiological role for aeroallergens and eosinophils in experimental eosinophilic esophagitis," *J Clin Invest* 2001, 107: 83-90.

O'Donnell M C et al., "Activation of basophil and mast cell histamine release by eosinophil granule major basic protein," *J Exp Med,* 1983, 157: 1981-1991.

Odze, R. D., "Pathology of eosinophilic esophagitis: What the clinician needs to know," *Am J Gastroenterol* 2009, 104: 485-490.

Pasha, S F, et al., "Patient characteristics, clinical, endoscopic, and histologic findings in adult eosinophilic esophagitis: a case series and systematic review of the medical literature," *Dis Esophagus* 2007, 20(4): 311-319.

Pentiuk, S et al., "Dissociation between symptoms and histological severity in pediatric eosinophilic esophagitis," *J Pediatr Gastroenterol Nutr.* 2009, 48: 152-160.

Peters M S et al., "Localization of human eosinophil granule major basic protein, eosinophil cationic protein, and eosinophil-derived neurotoxin by immunoelectron microscopy," *Lab Invest* 1986, 54: 656-662.

Peterson K A, et al., "Elemental Diet Induces Histologic Response in Adult Eosinophilic Esophagitis," *Am J Gastroenterol* 2013, Epub ahead of print.

Prasad, G A et al., "Secular trends in the epidemiology and outcomes of eosinophilic esophagitis in Olmsted County, Minn. (1976-2007)," *Digestive Disease Week, May* 2008.

Saffari H, et al., "Patchy eosinophil distributions in an esophagectomy specimen from a patient with eosinophilic esophagitis: Implications for endoscopic biopsy," *J Allergy Clin. Immunol.* 2012, 130: 798-800.

Shah, A et al., "Histopathologic variability in Children with Eosinophilic Esophagitis," *Am J Gastroenterol* 2009, 104(3): 716-721.

Straumann A, et al., "Natural history of primary eosinophilic esophagitis: a follow-up of 30 adult patients for up to 11.5 years," *Gastroenterology* 2003, 125: 1660-1669.

Swaminathan, G J et al., "Eosinophil-granule major basic protein, a C-type lectin, binds heparin," *Biochem* 2006, 44: 14152-14158.

Talley N J, Kephart G M, McGovern T W, Carpenter H A, Gleich G J., "Deposition of eosinophil granule major basic protein in eosinophilic gastroenteritis and celiac disease," *Gastroenterology.* 1992, 103: 137-145.

Tantibhaedhyangkul, U et al., "Increased Esophageal Regulatory T Cells and Eosinophil Characteristics in Children with Eosinophilic Esophagitis and Gastroesophageal Reflux Disease," *Annals of Clinical & Laboratory Science* 2009, 39: 99-107.

Wagner, L et al., "Eosinophils," *Encyclopedia of Life Sciences*, John Wiley & Sons 2006.

Wang F Y et al., "Is there a seasonal variation in the incidence or intensity of allergic eosinophilic esophagitis in newly diagnosed children?" *J Clin Gastroenterol Hepatol* 2007, 41: 451-453.

Wasmoen, T L et al., "Biochemical and amino acid sequence analysis of human eosinophil granule major basic protein," *J Biol Chem* 1988, 263: 12559-12563.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of producing a medical image of an esophagus in a subject, said method comprising:

administering to a subject radiolabeled heparin wherein the radiolabeled heparin binds to one or more eosinophil granule proteins in the mucosal tissue of the subject's esophagus, wherein said binding generates a radiolabeled heparin eosinophil granule protein complex, wherein the eosinophil granule protein is major basic protein 1 (MBP-1), major basic protein 2 (MBP-2), eosinophil derived neurotoxin (EDN), eosinophil cationic protein (ECP), or eosinophil peroxidase (EPO), and detecting the radiolabeled heparin eosinophil granule protein complex in the mucosal tissue of the subject's esophagus, whereby detecting the radiolabeled heparin eosinophil granule protein complex in the mucosal tissue of the esophagus produces a medical image of the esophagus in the subject.

2. The method of claim 1, wherein the radiolabel is $^{99m}$Tc.

3. The method of claim 1, wherein the radiolabeled heparin is administered to the subject orally.

4. The method of claim 1, wherein the subject is a human.

5. The method of claim 1, wherein the radiolabeled heparin eosinophil granule protein complex is detected using one or more of single-photon emission computed tomography (SPECT), positron emission tomography (PET) scans, X-ray, conventional or computed tomography (CT), a combination of SPECT and CT, or magnetic resonance imaging (MM).

6. A method of diagnosing eosinophilic esophagitis in a subject, the method comprising:
administering to a subject radiolabeled heparin wherein the radiolabeled heparin binds to one or more eosinophil granule proteins in the mucosal tissue of the subject's esophagus, wherein said binding generates a radiolabeled heparin eosinophil granule protein complex, wherein the eosinophil granule protein is major basic protein 1 (MBP-1), major basic protein 2 (MBP-2), eosinophil derived neurotoxin (EDN), eosinophil cationic protein (ECP), or eosinophil peroxidase (EPO), and
detecting the radiolabeled heparin eosinophil granule protein complex in the mucosal tissue of the esophagus,
whereby detecting the radiolabeled heparin eosinophil granule protein complex in the mucosal tissue of the esophagus diagnoses eosinophilic esophagitis in the subject.

7. The method of claim 6, wherein the radiolabeled heparin is administered to the subject orally.

8. The method of claim 6, wherein the subject is a human.

9. The method of claim 6, wherein the radiolabeled heparin eosinophil protein complex is detected using one or more of SPECT, PET scans, X-ray, conventional or computed tomography (CT), a combination of SPECT and CT, or MRI.

10. A method of detecting a change in eosinophilic esophagitis in a subject diagnosed with eosinophilic esophagitis, comprising:
a) producing a first medical image of the esophagus in a subject diagnosed with eosinophilic esophagitis according to the method of claim 1;
b) producing a second medical image of the esophagus in the subject of step (a), according to the method of claim 1; and
c) comparing the medical image of step (b) with the medical image of step (a), whereby detecting a change in the medical image of step (b) compared to the medical image of step (a) detects a change in eosinophilic esophagitis in the subject.

11. A method of detecting eosinophil degranulation in a subject, the method comprising:
administering to a subject radiolabeled heparin wherein the radiolabeled heparin binds to one or more eosinophil granule proteins in the mucosal tissue of the subject's esophagus, wherein said binding generates a radiolabeled heparin eosinophil granule protein complex, wherein the eosinophil granule protein is major basic protein 1 (MBP-1), major basic protein 2 (MBP-2), eosinophil derived neurotoxin (EDN), eosinophil cationic protein (ECP), or eosinophil peroxidase (EPO), and
detecting the radiolabeled heparin eosinophil granule protein complex in the mucosal tissue of the subject's esophagus,
whereby detecting the radiolabeled heparin eosinophil granule protein complex in the mucosal tissue of the esophagus detects eosinophil degranulation in the subject.

12. The method of claim 11, wherein the radiolabel is $^{99m}Tc$.

13. The method of claim 11, wherein the radio labeled heparin is administered to the subject orally.

14. The method of claim 11, wherein the subject is a human.

15. The method of claim 11, wherein the radiolabeled heparin eosinophil granule protein complex is detected using one or more of SPECT, PET scans, X-ray, conventional or computed tomography (CT), a combination of SPECT and CT, or MRI.

* * * * *